United States Patent
Stevens et al.

(10) Patent No.: US 9,856,521 B2
(45) Date of Patent: *Jan. 2, 2018

(54) LIGATION ASSAYS IN LIQUID PHASE

(71) Applicant: BioSpyder Technologies, Inc., Carlsbad, CA (US)

(72) Inventors: Anthony Stevens, San Diego, CA (US); Bruce Seligmann, Tuscon, AZ (US); Joanne M. Yeakley, Encinitas, CA (US); Joel McComb, Rancho Santa Fe, CA (US)

(73) Assignee: BioSpyder Technologies, Inc., Carlsbad, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/788,670

(22) Filed: Jun. 30, 2015

(65) Prior Publication Data

US 2016/0222447 A1 Aug. 4, 2016

Related U.S. Application Data

(60) Provisional application No. 62/108,161, filed on Jan. 27, 2015.

(51) Int. Cl.
*C12Q 1/68* (2006.01)
*C07H 21/00* (2006.01)

(52) U.S. Cl.
CPC ................. *C12Q 1/6827* (2013.01)

(58) Field of Classification Search
CPC .... C12Q 1/68; C12Q 1/686; C12Q 2521/319; C12Q 2521/501; C12P 19/34; C07H 21/00

See application file for complete search history.

(56) References Cited

U.S. PATENT DOCUMENTS

| | | | | |
|---|---|---|---|---|
| 4,988,617 A * | 1/1991 | Landegren | ............ | C12Q 1/6827 435/6.11 |
| 5,225,324 A * | 7/1993 | McFadden | ............. | C12Q 1/689 435/29 |
| 5,691,146 A * | 11/1997 | Mayrand | ................ | C07H 21/04 435/5 |
| 5,871,921 A * | 2/1999 | Landegren | ............ | C12Q 1/6813 435/6.1 |
| 6,027,889 A | 2/2000 | Barany et al. | | |
| 6,368,801 B1 * | 4/2002 | Faruqi | .................. | C12Q 1/6844 435/6.1 |
| 7,312,039 B2 | 12/2007 | Barany et al. | | |
| 7,320,865 B2 | 1/2008 | Barany et al. | | |
| 7,429,453 B2 | 9/2008 | Barany et al. | | |
| 8,597,891 B2 | 12/2013 | Barany et al. | | |
| 8,741,564 B2 | 6/2014 | Seligmann | | |
| 2003/0083273 A1 * | 5/2003 | Woolf | .................. | C12N 15/113 514/44 A |
| 2003/0104378 A1 * | 6/2003 | Allawi | ................. | C12N 9/1252 435/6.18 |
| 2004/0137484 A1 * | 7/2004 | Zhang | .................... | C12Q 1/682 435/6.11 |
| 2005/0026166 A1 | 2/2005 | Bi | | |
| 2006/0121452 A1 * | 6/2006 | Dhallan | ............... | C12Q 1/6827 435/5 |
| 2006/0246475 A1 | 11/2006 | Peterson et al. | | |
| 2007/0065816 A1 * | 3/2007 | Dong | .................. | C12Q 1/6809 435/6.11 |
| 2007/0275375 A1 * | 11/2007 | Van Eijk | ............. | C12Q 1/6844 435/6.11 |
| 2008/0182239 A1 * | 7/2008 | Mullinax | ............. | C12Q 1/6811 435/6.14 |
| 2008/0227104 A1 * | 9/2008 | Hayashizaki | ........ | C12Q 1/6853 435/6.11 |
| 2009/0203085 A1 * | 8/2009 | Kurn | ...................... | C12Q 1/686 435/91.2 |
| 2014/0141418 A1 * | 5/2014 | Park | ..................... | C12Q 1/6844 435/6.11 |
| 2014/0227683 A1 * | 8/2014 | Cobb | .................. | C12Q 1/6818 435/5 |
| 2014/0227691 A1 * | 8/2014 | May | ..................... | C12Q 1/6806 435/6.11 |
| 2014/0287468 A1 * | 9/2014 | Richard | .............. | C12Q 1/6806 435/91.53 |
| 2015/0038336 A1 * | 2/2015 | Barany | ................ | C12Q 1/6806 506/2 |
| 2016/0068886 A1 | 3/2016 | Yeakley et al. | | |
| 2016/0068907 A1 | 3/2016 | Shepard et al. | | |
| 2017/0101671 A1 | 4/2017 | Stevens et al. | | |

FOREIGN PATENT DOCUMENTS

CA    2914367 A1    12/2014

OTHER PUBLICATIONS

Ahern, H. The Scientist 9 (15) : 20 (1995).*
Barany, F. The ligase chain reaction in a PCR world. PCR Methods and Applications 1 : 5-16 (1991).*
Cai et al., Human microRNAs are processed from capped, polyadenylated transcripts that can also function as mRNAs.RNA 10 : 1957 (2004).*
Hsuih et al., Novel, Ligation-Dependent PCR Assay for Detection of Hepatitis C Virus in Serum. J. of Clinical Microbiology34 (3) : 501 (1996).*
Pritchard et al., MicroRNA profiling : approaches and considerations. Nature Reviews Genetics 13 :358 (2012).*
Schouten et al., Relative quantification of 40 nucleic acid sequences by multiplex ligation-dependent probe amplification. Nucleic Acids Research 30 (12) : e57 (2002).*
Shevelev et al., The 3'-5' Exonucleases. Nature Reviews Molecular Cell Biology 3 :1 (2002).*
Shi et al.,Facile means for quantifying microRNA expression by real-time PCR. BioTechniques 39 (4) : 519 (2005).*
Vallone et al., qPCR Workshop hald Jul. 26-27, 2006.at NFSTC—Presentation slides.*
Vrettou et al., Real-Time PCR for Single-Cell Genotyping in Sickle Cell and Thalassemia Syndromes as a Rapid, Accurate, Reliable, and Widely Applicable Protocol for Preimplantation Genetic Diagnosis. Human Mutation 23 : 513 (2004).*

(Continued)

*Primary Examiner* — Ethan C Whisenant

(57) ABSTRACT

Ligation assays in liquid phase for detecting nucleic acid sequences.

60 Claims, 11 Drawing Sheets

(56) References Cited

OTHER PUBLICATIONS

Wiedmann et al., Ligase chain reaction (LCR)—overview and applications. PCR Methods and Applications 1 : 5-16 (1991)*
Chun et al., Dual priming oligonucleotide system for the multiplex detection of respiratory viruses and SNP genotyping of CYP2C19 gene. Nucleic Acids Research 35(6) : e40 (2007).*
Hwang et al., Biotechniques 35(6) : 1180 (2003).Sanger et al.PNAS 74(12) : 5463 (1977).*
Sanger et al. 74 (12) : 5463 (1977).*
International Search Report and Written Opinion mailed by ISA/US dated Apr. 14, 2016 for related application PCT/US16/14999.
Response to second Examination Report in UK sister application, with 3rd set of replacement claims, dated May 3, 2017.
Intention to Grant UK patent, dated May 23, 2017.
Replacement claims for foreign counterpart GB 1 614 871.0, filed in UK IPO, Aug. 31, 2016.
First Examination Report, dated Oct. 14, 2016.
Response to first Examination Report, dated Dec. 13, 2016, with 2nd set of replacement claims.
Second Examination Report, dated Feb. 27, 2017.

* cited by examiner

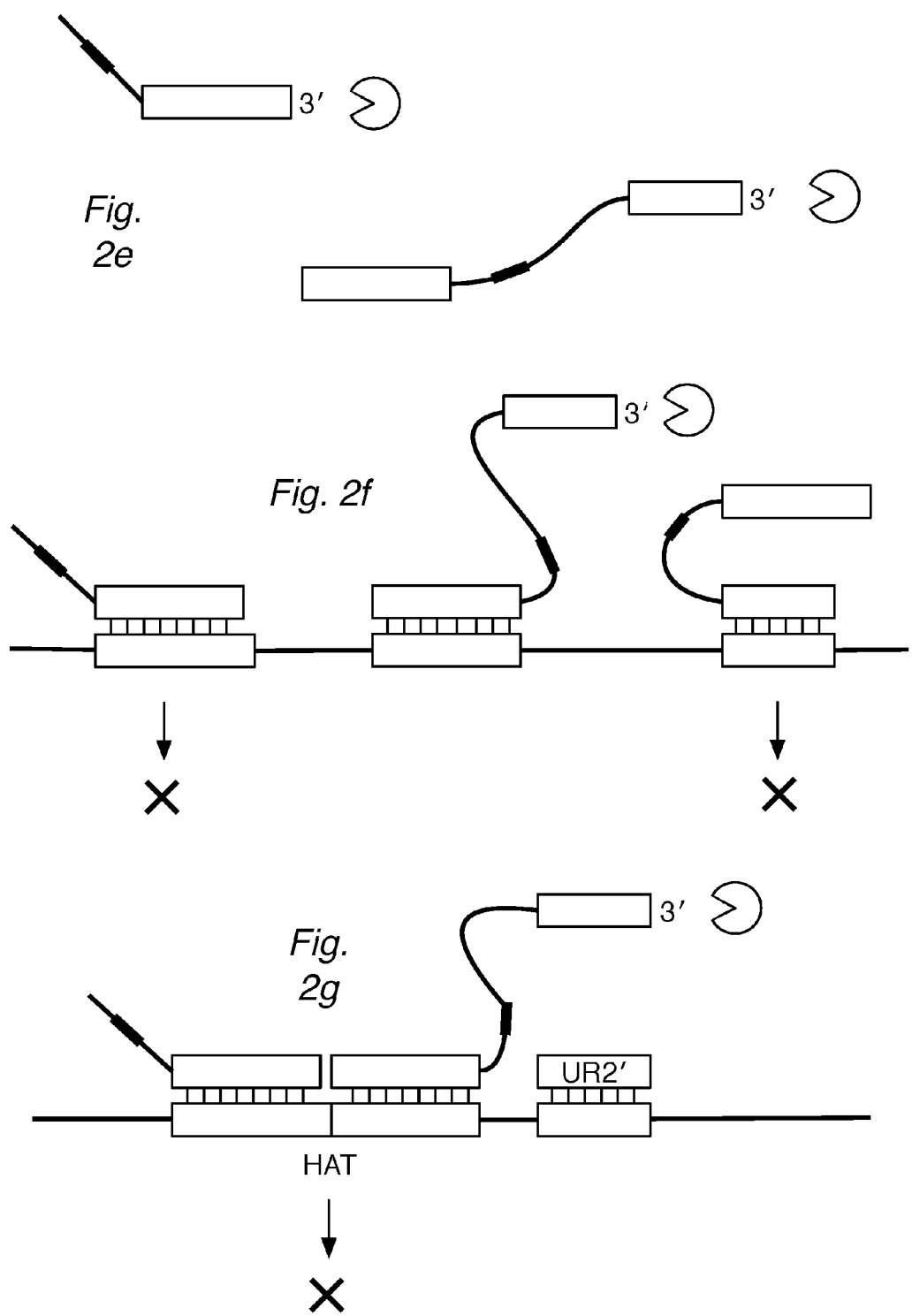

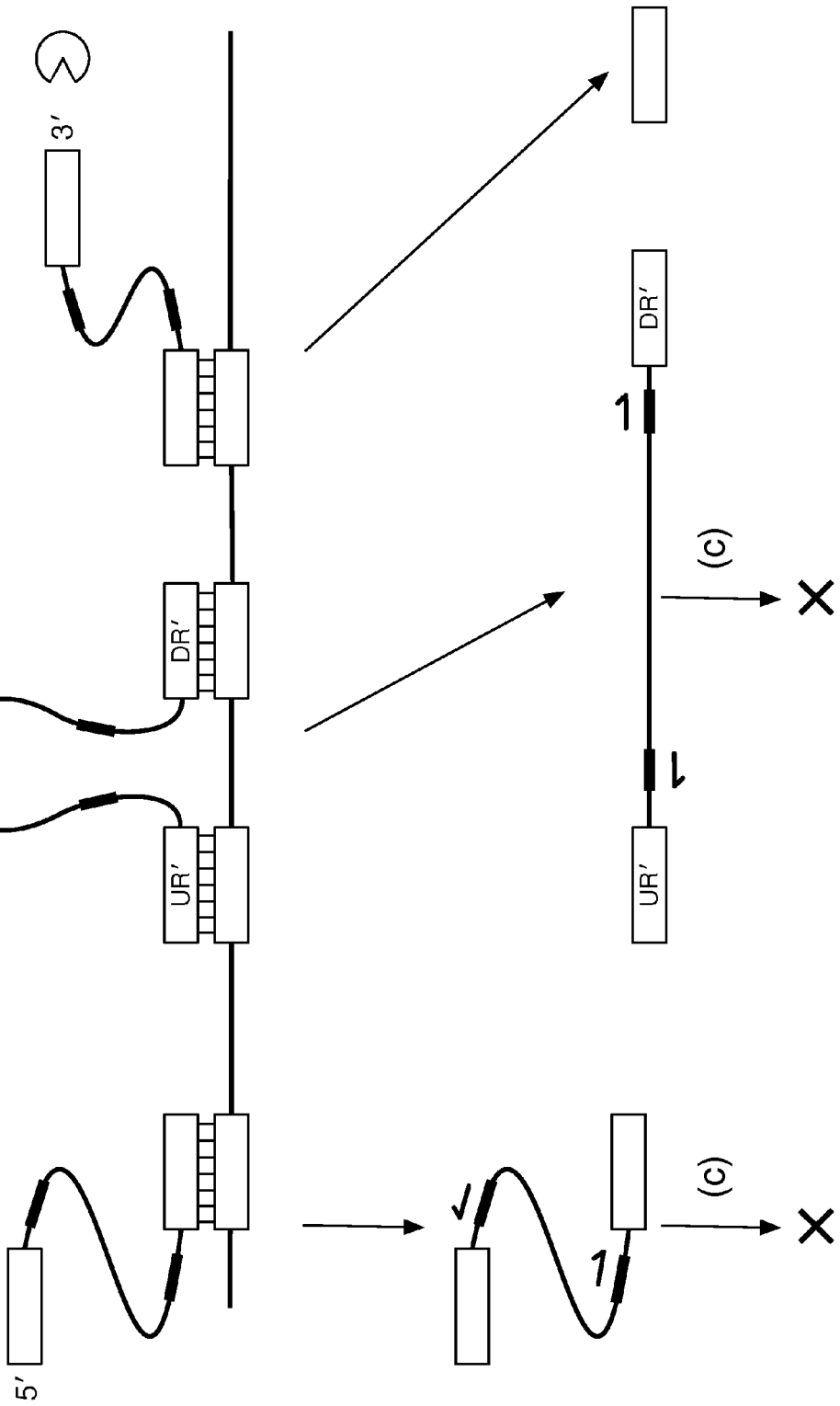

Figure 6a

| gene | DR' and UR' of detectors | |
|---|---|---|
| ACTB_1 | AGGTGTGCACTTTTATTCAACTGGTCTCAAGTCAGTGTACAGGTAAGCCC | SEQ ID NO:33 |
| BAD_3 | CGAGGAAGTCCCTTCTTAAAGGAGTCCACAAACTCGTCACTCATCCTCCG | SEQ ID NO:34 |
| BCAT2_3 | CTTGTCATTCCATTCCACCATCAGCATGTGGTCGGTAAATGTCTTCCCAA | SEQ ID NO:35 |
| BMP4_1 | GTGTATATCTGTCTATCCTCAAGGACTGCCTGATCTCAGCGGCACCCACA | SEQ ID NO:36 |
| BRCA1_2 | TGCCCAAGGACTATTCTGACTTTAAGTCACATAATCGATCCCAAGCACTC | SEQ ID NO:37 |
| BRCA2_1 | TTCTTCCGTACTGGCCTGGGAACTCTCCTGTTCTTTGATCAGAGATGTAG | SEQ ID NO:38 |
| CDH1_1 | TATTCTCGGTTTTCTGTGCACACCTGGAATTGGGCAAATGTGTTCAGCTC | SEQ ID NO:39 |
| EGF_3 | TTTTCCATCCCCAGCAAATCCTTTCAAACACTGACATGTGGCATCCTCTC | SEQ ID NO:40 |
| EGFR_1 | AGCAAAAGGAACATTTTGTATGTGTGTGTGACTGAACATAACTGTAGGCT | SEQ ID NO:41 |
| ESR1_1 | GCGACAAAACCGAGTCACATCAGTAATAGTATGCATCGGCAAAAGGGCAT | SEQ ID NO:42 |
| GAPDH_3 | CCATTGATGACAAGCTTCCCGTTCTCAGCCTTGACGGTGCCATGGAATTT | SEQ ID NO:43 |
| GATA3_3 | CTCTCTGAAACCCTCAACGGCAACTGGTGAACGGTAACACTGATTGCCCA | SEQ ID NO:44 |
| ICAM1_2 | CTGGCATCCGTCAGGAAGTGTGGGCCTTTGTGTTTTGATGCTACACATGT | SEQ ID NO:45 |
| IGF2_3 | CCCTGCCCCAGCCTGATGGAACCCTCTGTTTACACACCTGCTAGCCCCTT | SEQ ID NO:46 |
| KIT_3 | TGAGCCTATTCTCACAGATCTCCTTTTGTCGGCCTTGGTTGGGACAACAT | SEQ ID NO:47 |
| KRT19_2 | TCCGTTTCTGCCAGTGTGTCTTCCAAGGCAGCTTTCATGCTCAGCTGTGA | SEQ ID NO:48 |
| LAMP1_2 | CTTTGAATATATTGACTGAAAACGUCTTCGTGACACGGACGTGCTCCTCC | SEQ ID NO:49 |
| MUC1_3 | ATCGAGAGGCTGCTTCCGTTTTATACTGATTGAACTGTGTCTCCACGTCG | SEQ ID NO:50 |
| NFKBIA_1 | TACATTATGTACACCATTTACAGGAGGGTAACACAAACCTTGACAGGTAG | SEQ ID NO:51 |
| PTEN_1 | TGCATAGCATTTACACACAGAGCCACTGCTGCACAGCACAAGAGTATCTG | SEQ ID NO:52 |
| TFF1_1 | AAGCGTGTCTGAGGTGTCCGGTGGAGGTGGCAGCCGAGCTCTGGGACTAA | SEQ ID NO:53 |
| TIMP1_2 | GCATCCCCTAAGGCTTGGAACCCTUTATACATCTTGGTCATCTTGATCTC | SEQ ID NO:54 |
| VEGFA_3 | GATGGTGTGGTGGCGGCAGCGTGGTTTCTGTATCGATCGTTCTGTATCAG | SEQ ID NO:55 |
| WNT1_1 | AGGAGCCGCTAATAGCTACAGTGGAAGGAAATACTGATTCCAGGAGGCAA | SEQ ID NO:56 |

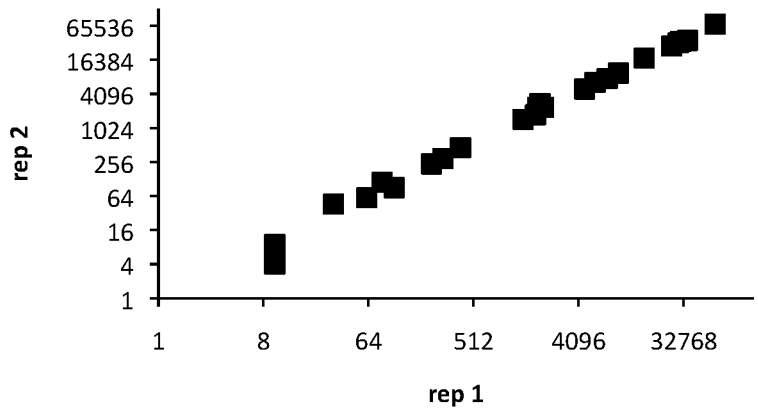
Fig. 6b: Anchored probes, 10 ng input
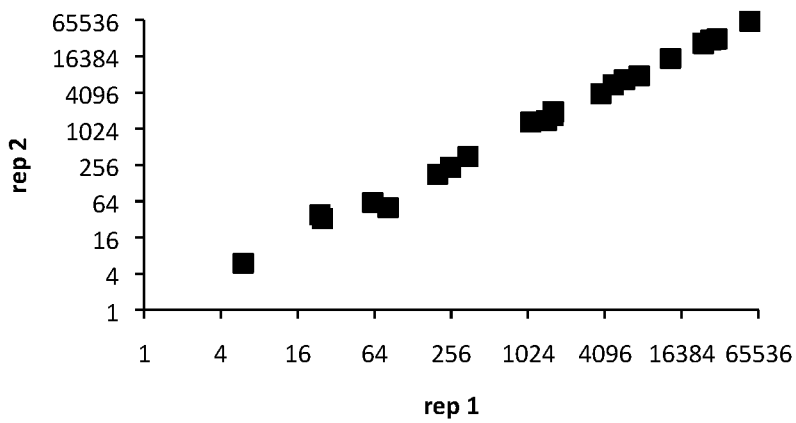
Fig. 6c: Anchored probes, 1 ng input
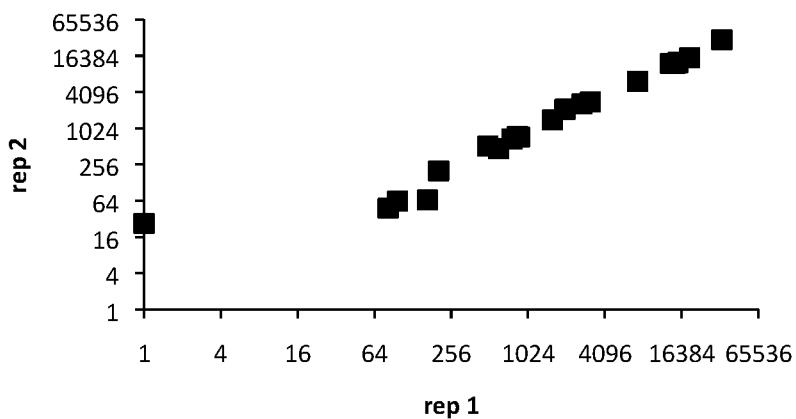
Fig. 6d: Anchored probes, 0.1 ng input

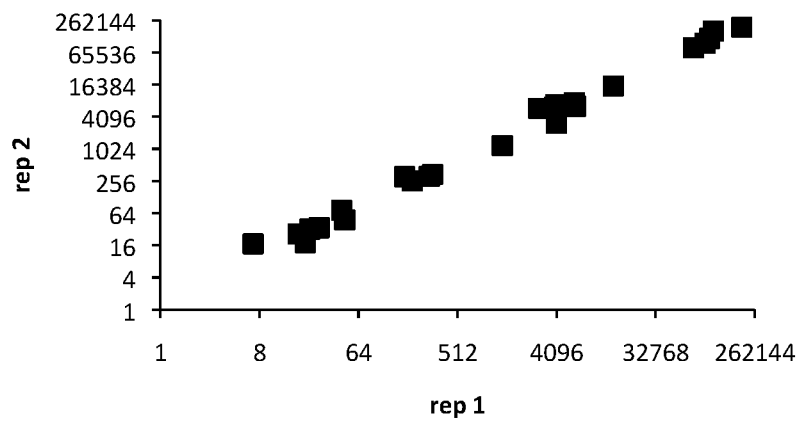
Fig. 6e: Circular probe, 10 ng input
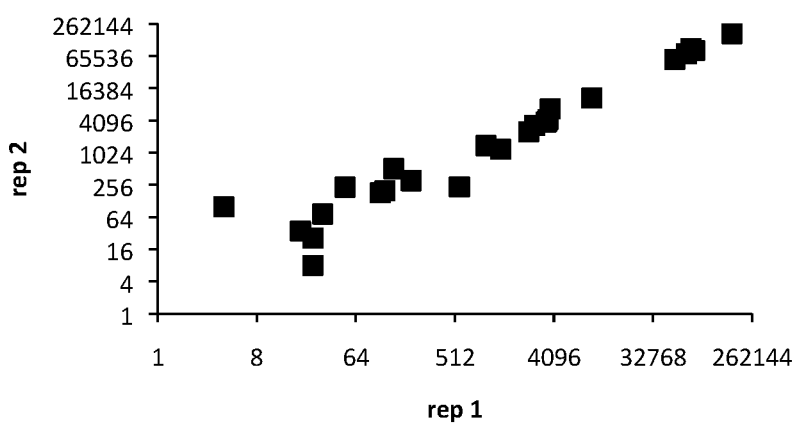
Fig. 6f: Circular probe, 1 ng input
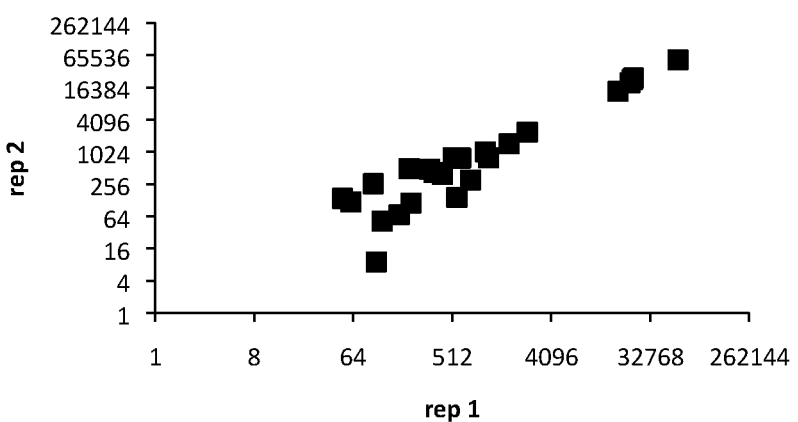
Fig. 6g: Circular probe, 0.1 ng input

SEQUENCE LISTING

```
<160> NUMBER OF SEQ ID NOS: 56

<210> SEQ ID NO 1
<211> LENGTH: 22
<212> TYPE: DNA
<213> ORGANISM: Artificial Sequence
<220> FEATURE:
<223> OTHER INFORMATION: synthetic downstream amplification sequence
      (P1)

<400> SEQUENCE: 1
caagcagaag acggcatacg ag                                             22

<210> SEQ ID NO 2
<211> LENGTH: 23
<212> TYPE: DNA
<213> ORGANISM: Artificial Sequence
<220> FEATURE:
<223> OTHER INFORMATION: synthetic upstream amplification sequence (P2')

<400> SEQUENCE: 2
atctcggtgg tcgccgtatc att                                            23

<210> SEQ ID NO 3
<211> LENGTH: 23
<212> TYPE: DNA
<213> ORGANISM: Artificial Sequence
<220> FEATURE:
<223> OTHER INFORMATION: synthetic amplification primer (P2)

<400> SEQUENCE: 3
aatgatacgg cgaccaccga gat                                            23

<210> SEQ ID NO 4
<211> LENGTH: 50
<212> TYPE: RNA
<213> ORGANISM: Homo sapiens

<400> SEQUENCE: 4
cgaccacuuu gucaagcuca uuuccuggua ugacaacgaa uuuggcuaca               50

<210> SEQ ID NO 5
<211> LENGTH: 50
<212> TYPE: RNA
<213> ORGANISM: Homo sapiens

<400> SEQUENCE: 5
cgaccacuuu gucaagcuca uuuccuggua ugacaacgaa uuuggcuaca               50
```

```
<210> SEQ ID NO 6
<211> LENGTH: 25
<212> TYPE: RNA
<213> ORGANISM: Homo sapiens

<400> SEQUENCE: 6
ugguaugaca acgaauuugg cuaca                                            25

<210> SEQ ID NO 7
<211> LENGTH: 25
<212> TYPE: DNA
<213> ORGANISM: Homo sapiens

<400> SEQUENCE: 7
tgtagccaaa ttcgttgtca tacca                                            25

<210> SEQ ID NO 8
<211> LENGTH: 25
<212> TYPE: RNA
<213> ORGANISM: Homo sapiens

<400> SEQUENCE: 8
cgaccacuuu gucaagcuca uuucc                                            25

<210> SEQ ID NO 9
<211> LENGTH: 25
<212> TYPE: DNA
<213> ORGANISM: Homo sapiens

<400> SEQUENCE: 9
ggaaatgagc ttgacaaagt ggtcg                                            25

<210> SEQ ID NO 10
<211> LENGTH: 22
<212> TYPE: RNA
<213> ORGANISM: Homo sapiens

<400> SEQUENCE: 10
ugagguagua gguuguauag uu                                               22

<210> SEQ ID NO 11
<211> LENGTH: 22
<212> TYPE: RNA
<213> ORGANISM: Homo sapiens

<400> SEQUENCE: 11
ugagguagua gguugugugg uu                                               22

<210> SEQ ID NO 12
<211> LENGTH: 22
<212> TYPE: RNA
<213> ORGANISM: Homo sapiens

<400> SEQUENCE: 12
ugagguagua gguuguaugg uu                                               22

<210> SEQ ID NO 13
<211> LENGTH: 22
<212> TYPE: RNA
<213> ORGANISM: Homo sapiens

<400> SEQUENCE: 13
agagguagua gguugcauag uu                                               22
```

```
<210> SEQ ID NO 14
<211> LENGTH: 22
<212> TYPE: RNA
<213> ORGANISM: Homo sapiens

<400> SEQUENCE: 14
ugagguagga gguuguauag uu                                            22

<210> SEQ ID NO 15
<211> LENGTH: 22
<212> TYPE: RNA
<213> ORGANISM: Homo sapiens

<400> SEQUENCE: 15
ugagguagua gauuguauag uu                                            22

<210> SEQ ID NO 16
<211> LENGTH: 22
<212> TYPE: RNA
<213> ORGANISM: Homo sapiens

<400> SEQUENCE: 16
ugagguagua guuuguacag uu                                            22

<210> SEQ ID NO 17
<211> LENGTH: 22
<212> TYPE: RNA
<213> ORGANISM: Homo sapiens

<400> SEQUENCE: 17
ugagguagua guuugugcug uu                                            22

<210> SEQ ID NO 18
<211> LENGTH: 11
<212> TYPE: DNA
<213> ORGANISM: Homo sapiens

<400> SEQUENCE: 18
aactatacaa c                                                        11

<210> SEQ ID NO 19
<211> LENGTH: 11
<212> TYPE: DNA
<213> ORGANISM: Homo sapiens

<400> SEQUENCE: 19
ctactacctc a                                                        11

<210> SEQ ID NO 20
<211> LENGTH: 34
<212> TYPE: DNA
<213> ORGANISM: Artificial Sequence
<220> FEATURE:
<223> OTHER INFORMATION: DNA reverse complement for human let-7a
      flanked by synthetic 2S sequences, as hybridized

<400> SEQUENCE: 20
taagagaact atacaaccta ctacctcacg gaac                               34

<210> SEQ ID NO 21
<211> LENGTH: 34
<212> TYPE: DNA
<213> ORGANISM: Artificial Sequence
<220> FEATURE:
```

-continued

<223> OTHER INFORMATION: human let-7a microRNA flanked by synthetic 2S
      DNA sequences, as hybridized

<400> SEQUENCE: 21
gttccgugag guaguagguu guauaguuct ctta                              34

<210> SEQ ID NO 22
<211> LENGTH: 34
<212> TYPE: DNA
<213> ORGANISM: Artificial Sequence
<220> FEATURE:
<223> OTHER INFORMATION: DNA reverse complement for human let-7a flanked
      by synthetic 2S sequences, as ligated detector oligo (DO)

<400> SEQUENCE: 22
taagagaact atacaaccta ctacctcacg gaac                              34

<210> SEQ ID NO 23
<211> LENGTH: 34
<212> TYPE: DNA
<213> ORGANISM: Artificial Sequence
<220> FEATURE:
<223> OTHER INFORMATION: human let-7a microRNA flanked by synthetic 2S
      DNA sequences, as ligated

<400> SEQUENCE: 23
gttccgugag guaguagguu guauaguuct ctta                              34

<210> SEQ ID NO 24
<211> LENGTH: 34
<212> TYPE: DNA
<213> ORGANISM: Artificial Sequence
<220> FEATURE:
<223> OTHER INFORMATION: DNA reverse complement of human let-7a flanked
      by synthetic 2S sequences, as ligated detector oligo (DO)

<400> SEQUENCE: 24
taagagaact atacaaccta ctacctcacg gaac                              34

<210> SEQ ID NO 25
<211> LENGTH: 34
<212> TYPE: DNA
<213> ORGANISM: Artificial Sequence
<220> FEATURE:
<223> OTHER INFORMATION: human let-7c microRNA flanked by synthetic DNA
      2S sequences, as ligated

<400> SEQUENCE: 25
gttccgugag guaguagguu guaugguuct ctta                              34

<210> SEQ ID NO 26
<211> LENGTH: 16
<212> TYPE: DNA
<213> ORGANISM: Artificial Sequence
<220> FEATURE:
<223> OTHER INFORMATION: DNA complement of downstream region (DR') for
      human let-7a, extended with synthetic poly-dT region

<400> SEQUENCE: 26
ttttttttaa ctatac                                                  16

<210> SEQ ID NO 27
<211> LENGTH: 14
<212> TYPE: DNA
<213> ORGANISM: Homo sapiens

<400> SEQUENCE: 27

```
aacctactac ctca                                                         14

<210> SEQ ID NO 28
<211> LENGTH: 27
<212> TYPE: RNA
<213> ORGANISM: Artificial Sequence
<220> FEATURE:
<223> OTHER INFORMATION: human let-7a microRNA supplemented by synthetic
      poly-A tail

<400> SEQUENCE: 28
ugagguagua gguuguauag uuaaaaa                                           27

<210> SEQ ID NO 29
<211> LENGTH: 16
<212> TYPE: DNA
<213> ORGANISM: Artificial Sequence
<220> FEATURE:
<223> OTHER INFORMATION: DNA complement of downstream region (DR') for
      human let-7b, extended with synthetic poly-dT region

<400> SEQUENCE: 29
ttttttttaa ccacac                                                       16

<210> SEQ ID NO 30
<211> LENGTH: 27
<212> TYPE: RNA
<213> ORGANISM: Artificial Sequence
<220> FEATURE:
<223> OTHER INFORMATION: human let-7b microRNA supplemented by synthetic
      poly-A tail

<400> SEQUENCE: 30
ugagguagua gguugugugg uuaaaaa                                           27

<210> SEQ ID NO 31
<211> LENGTH: 22
<212> TYPE: DNA
<213> ORGANISM: Artificial Sequence
<220> FEATURE:
<223> OTHER INFORMATION: partial upstream portion of synthetic DNA
      detector (DO) with poly-A region (CP5)

<400> SEQUENCE: 31
aaaaactact acctcacgga ac                                                22

<210> SEQ ID NO 32
<211> LENGTH: 18
<212> TYPE: DNA
<213> ORGANISM: Artificial Sequence
<220> FEATURE:
<223> OTHER INFORMATION: partial downstream portion of synthetic DNA
      detector (DO) with noncomplementary region (CP3)

<400> SEQUENCE: 32
taagagaact atacaacc                                                     18

<210> SEQ ID NO 33
<211> LENGTH: 50
<212> TYPE: DNA
<213> ORGANISM: Homo sapiens

<400> SEQUENCE: 33
aggtgtgcac ttttattcaa ctggtctcaa gtcagtgtac aggtaagccc                  50
```

<210> SEQ ID NO 34
<211> LENGTH: 50
<212> TYPE: DNA
<213> ORGANISM: Homo sapiens

<400> SEQUENCE: 34
cgaggaagtc ccttcttaaa ggagtccaca aactcgtcac tcatcctccg        50

<210> SEQ ID NO 35
<211> LENGTH: 50
<212> TYPE: DNA
<213> ORGANISM: Homo sapiens

<400> SEQUENCE: 35
cttgtcattc cattccacca tcagcatgtg gtcggtaaat gtcttcccaa        50

<210> SEQ ID NO 36
<211> LENGTH: 50
<212> TYPE: DNA
<213> ORGANISM: Homo sapiens

<400> SEQUENCE: 36
gtgtatatct gtctatcctc aaggactgcc tgatctcagc ggcacccaca        50

<210> SEQ ID NO 37
<211> LENGTH: 50
<212> TYPE: DNA
<213> ORGANISM: Homo sapiens

<400> SEQUENCE: 37
tgcccaagga ctattctgac tttaagtcac ataatcgatc ccaagcactc        50

<210> SEQ ID NO 38
<211> LENGTH: 50
<212> TYPE: DNA
<213> ORGANISM: Homo sapiens

<400> SEQUENCE: 38
ttcttccgta ctggcctggg aactctcctg ttctttgatc agagatgtag        50

<210> SEQ ID NO 39
<211> LENGTH: 50
<212> TYPE: DNA
<213> ORGANISM: Homo sapiens

<400> SEQUENCE: 39
tattctcggt tttctgtgca cacctggaat tgggcaaatg tgttcagctc        50

<210> SEQ ID NO 40
<211> LENGTH: 50
<212> TYPE: DNA
<213> ORGANISM: Homo sapiens

<400> SEQUENCE: 40
ttttccatcc ccagcaaatc ctttcaaaca ctgacatgtg gcatcctctc        50

<210> SEQ ID NO 41
<211> LENGTH: 50
<212> TYPE: DNA
<213> ORGANISM: Homo sapiens

<400> SEQUENCE: 41
agcaaaagga acattttgta tgtgtgtgtg actgaacata actgtaggct        50

```
<210> SEQ ID NO 42
<211> LENGTH: 50
<212> TYPE: DNA
<213> ORGANISM: Homo sapiens

<400> SEQUENCE: 42
gcgacaaaac cgagtcacat cagtaatagt atgcatcggc aaaagggcat            50

<210> SEQ ID NO 43
<211> LENGTH: 50
<212> TYPE: DNA
<213> ORGANISM: Homo sapiens

<400> SEQUENCE: 43
ccattgatga caagcttccc gttctcagcc ttgacggtgc catggaattt            50

<210> SEQ ID NO 44
<211> LENGTH: 50
<212> TYPE: DNA
<213> ORGANISM: Homo sapiens

<400> SEQUENCE: 44
ctctctgaaa ccctcaacgg caactggtga acggtaacac tgattgccca            50

<210> SEQ ID NO 45
<211> LENGTH: 50
<212> TYPE: DNA
<213> ORGANISM: Homo sapiens

<400> SEQUENCE: 45
ctggcatccg tcaggaagtg tgggcctttg tgttttgatg ctacacatgt            50

<210> SEQ ID NO 46
<211> LENGTH: 50
<212> TYPE: DNA
<213> ORGANISM: Homo sapiens

<400> SEQUENCE: 46
ccctgcccca gcctgatgga accctctgtt tacacacctg ctagcccctt            50

<210> SEQ ID NO 47
<211> LENGTH: 50
<212> TYPE: DNA
<213> ORGANISM: Homo sapiens

<400> SEQUENCE: 47
tgagcctatt ctcacagatc tccttttgtc ggccttggtt gggacaacat            50

<210> SEQ ID NO 48
<211> LENGTH: 50
<212> TYPE: DNA
<213> ORGANISM: Homo sapiens

<400> SEQUENCE: 48
tccgtttctg ccagtgtgtc ttccaaggca gctttcatgc tcagctgtga            50

<210> SEQ ID NO 49
<211> LENGTH: 50
<212> TYPE: DNA
<213> ORGANISM: Homo sapiens

<400> SEQUENCE: 49
ctttgaatat attgactgaa aacgtcttcg tgacacggac gtgctcctcc            50
```

<210> SEQ ID NO 50
<211> LENGTH: 50
<212> TYPE: DNA
<213> ORGANISM: Homo sapiens

<400> SEQUENCE: 50
atcgagaggc tgcttccgtt ttatactgat tgaactgtgt ctccacgtcg        50

<210> SEQ ID NO 51
<211> LENGTH: 50
<212> TYPE: DNA
<213> ORGANISM: Homo sapiens

<400> SEQUENCE: 51
tacattatgt acaccattta caggagggta acacaaacct tgacaggtag        50

<210> SEQ ID NO 52
<211> LENGTH: 50
<212> TYPE: DNA
<213> ORGANISM: Homo sapiens

<400> SEQUENCE: 52
tgcatagcat ttacacacag agccactgct gcacagcaca agagtatctg        50

<210> SEQ ID NO 53
<211> LENGTH: 50
<212> TYPE: DNA
<213> ORGANISM: Homo sapiens

<400> SEQUENCE: 53
aagcgtgtct gaggtgtccg gtggaggtgg cagccgagct ctgggactaa        50

<210> SEQ ID NO 54
<211> LENGTH: 50
<212> TYPE: DNA
<213> ORGANISM: Homo sapiens

<400> SEQUENCE: 54
gcatccccta aggcttggaa ccctttatac atcttggtca tcttgatctc        50

<210> SEQ ID NO 55
<211> LENGTH: 50
<212> TYPE: DNA
<213> ORGANISM: Homo sapiens

<400> SEQUENCE: 55
gatggtgtgg tggcggcagc gtggtttctg tatcgatcgt tctgtatcag        50

<210> SEQ ID NO 56
<211> LENGTH: 50
<212> TYPE: DNA
<213> ORGANISM: Homo sapiens

<400> SEQUENCE: 56
aggagccgct aatagctaca gtggaaggaa atactgattc caggaggcaa        50

LIGATION ASSAYS IN LIQUID PHASE

CROSS-REFERENCE TO RELATED APPLICATIONS

This application claims the benefit of priority of provisional application 62/108,161, filed Jan. 27, 2015, the contents of which are incorporated herein in its entirety.

This invention was made with government support under grant 1R43HG007815 awarded by the National Institutes of Health. The government has certain rights in the invention.

TECHNICAL FIELD

This invention relates to molecular biology, and more particularly to assays for detecting nucleic acid sequences in samples.

SUMMARY OF THE INVENTION

This invention provides methods for detecting target nucleic acid sequences of interest in a sample, and also provides kits for performing the method.

In a typical ligation assay, the sample is contacted with a pool of detector oligos, where a downstream detector (DD) and an upstream detector (UD) are provided for each target sequence. A portion (DR') of the DD is complementary to a region of the target sequence designated as a downstream region (DR). The upstream detector has a portion (UR') complementary to an upstream region (UR) of the target sequence.

The downstream and upstream detectors are contacted with the sample and allowed to hybridize to the corresponding regions of target sequence present in the sample. When the detectors are specifically hybridized to a target sequence, they can be ligated at the junction between adjacent detectors, whether directly or after an optional extension step. Formation of a ligation product thus serves as evidence that the target sequence was present in the sample, and the ligation product can be detected by various methods such as detectable labels, microarrays, qPCR, flow-through counters, and sequencing.

The invention provides assays where one or more nucleases are provided during steps in the method to selectively degrade unused or excess detectors, or detectors that are not specifically hybridized to target sequences of interest. Accordingly, the detectors and other components of the assay are configured in a number of embodiments to resist the nucleases while detecting target sequences. The configurations enable sensitive detection of nucleic acids, such as mRNAs and miRNAs, at whole-transcriptome or -miRNome multiplexing and at the level of single cells. Moreover, the steps can be performed in a single well or container without the need for transfers, separation, or solid-phase immobilization, and are therefore ideal for microfluidic platforms.

Treatment with an exonuclease, such as an exonuclease with single-stranded 3'-to-5' activity, can be used at various stages of the method to remove undesired components, such as nonbound or excess DD and UD detectors as in FIG. 2e. Detectors that are nonspecifically or incompletely hybridized to target sequences can be degraded by the exonuclease or will not result in ligation or amplification product, as in FIG. 2f.

As shown in FIG. 2g, it may be desirable to provide predetermined quantities of attenuator oligonucleotides such as UR2' (or alternatively UR2) to lessen the formation of product resulting from certain high-abundance target sequences (HATs).

Figure 2A:
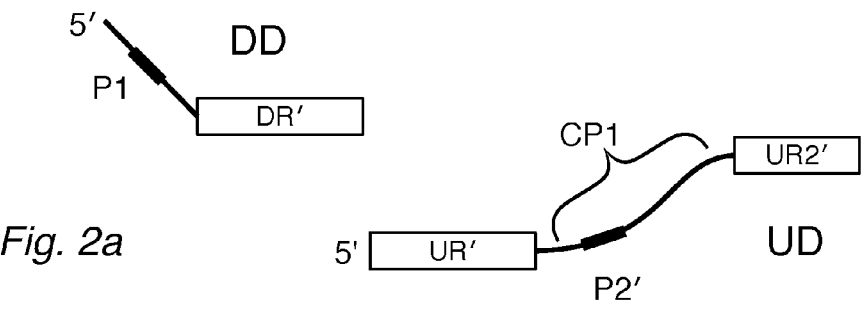
FIG. 2a shows an "anchored" assay design of the invention where the UD is configured with a second complementary region (UR2' or "anchor") separated by a noncomplementary region (CP1). The DD and UD can hybridize to a target sequence as in FIG. 2b, forming a hybridization complex (HC) providing a substrate for ligation at the junction (L) between DR' and UR'. After ligation.
Figure 2B:
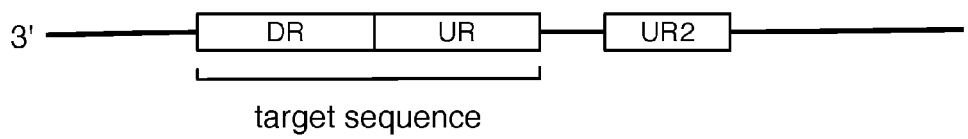
FIG. 2c shows the ligation product (LP) can be amplified by primers to yield amplification products (AP) in FIG. 2d.
Figure 2B:
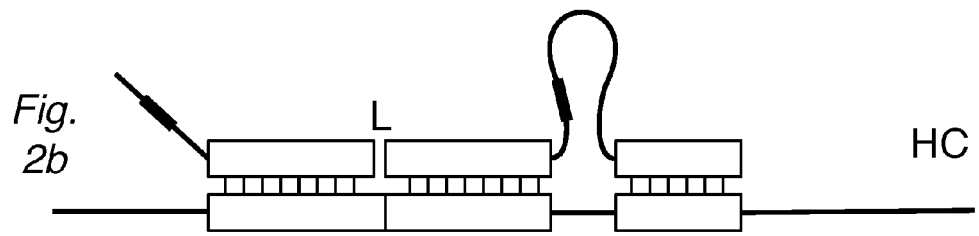
Figure 2C:
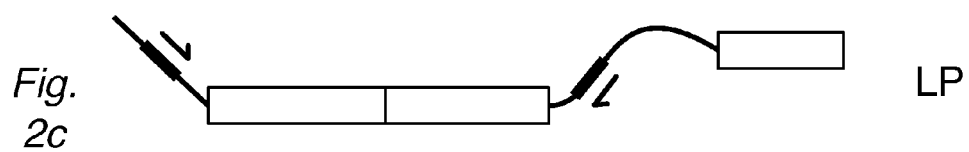
Figure 2D:
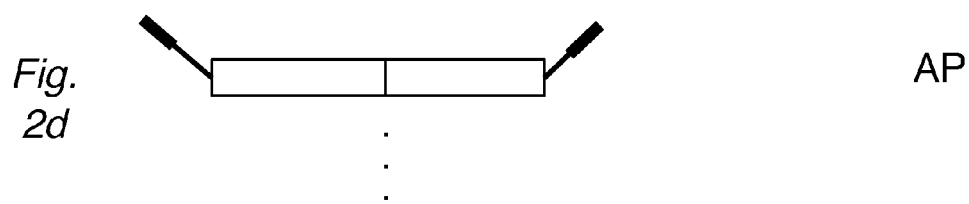
Figure 2H:
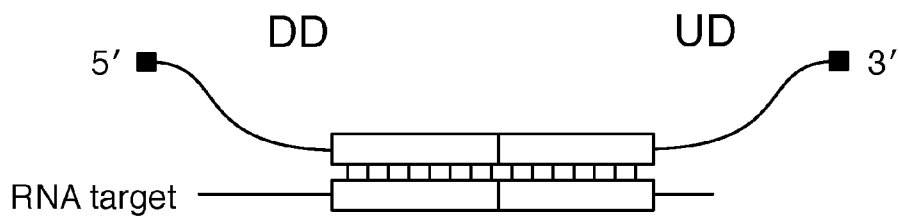

FIG. 2h shows a pair of detectors that are configured to have a modification at one end to resist exonucleases that degrade single-stranded (ss) DNA. The UD has a modification at the 3' end that resists degradation of the detector by an exonuclease having 3' activity on DNA single strands. Alternatively, the DD can have a 5' modification to resist degradation by a 5'-ss-exonuclease.

Figure 2I:
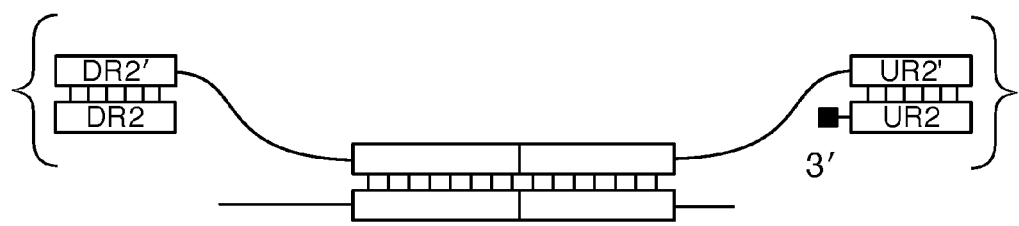
Figure 2J:
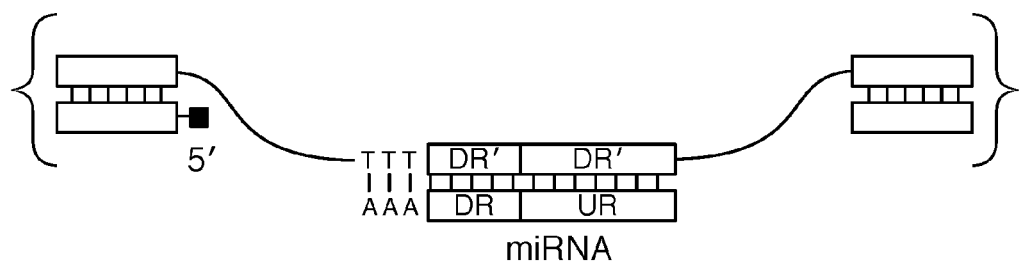

FIGS. 2i and 2j illustrate detectors that are configured to resist exonucleases by being hybridized to a protector oligo, such as ones having sequence DR2 or UR2 that bind to corresponding DR2' and UR2' sequences of the detectors, presenting double-stranded structures at either end. The protectors can themselves be 5'- or 3'-modified to resist exonucleases, as shown. FIG. 2j also illustrates a target sequence (3'-DR-UR-5') that is relatively short, such as a microRNA, where the target has been polyadenylated at its 3' end. The DD features a complementary poly-T portion adjacent to the DR'.

Figure 3A:
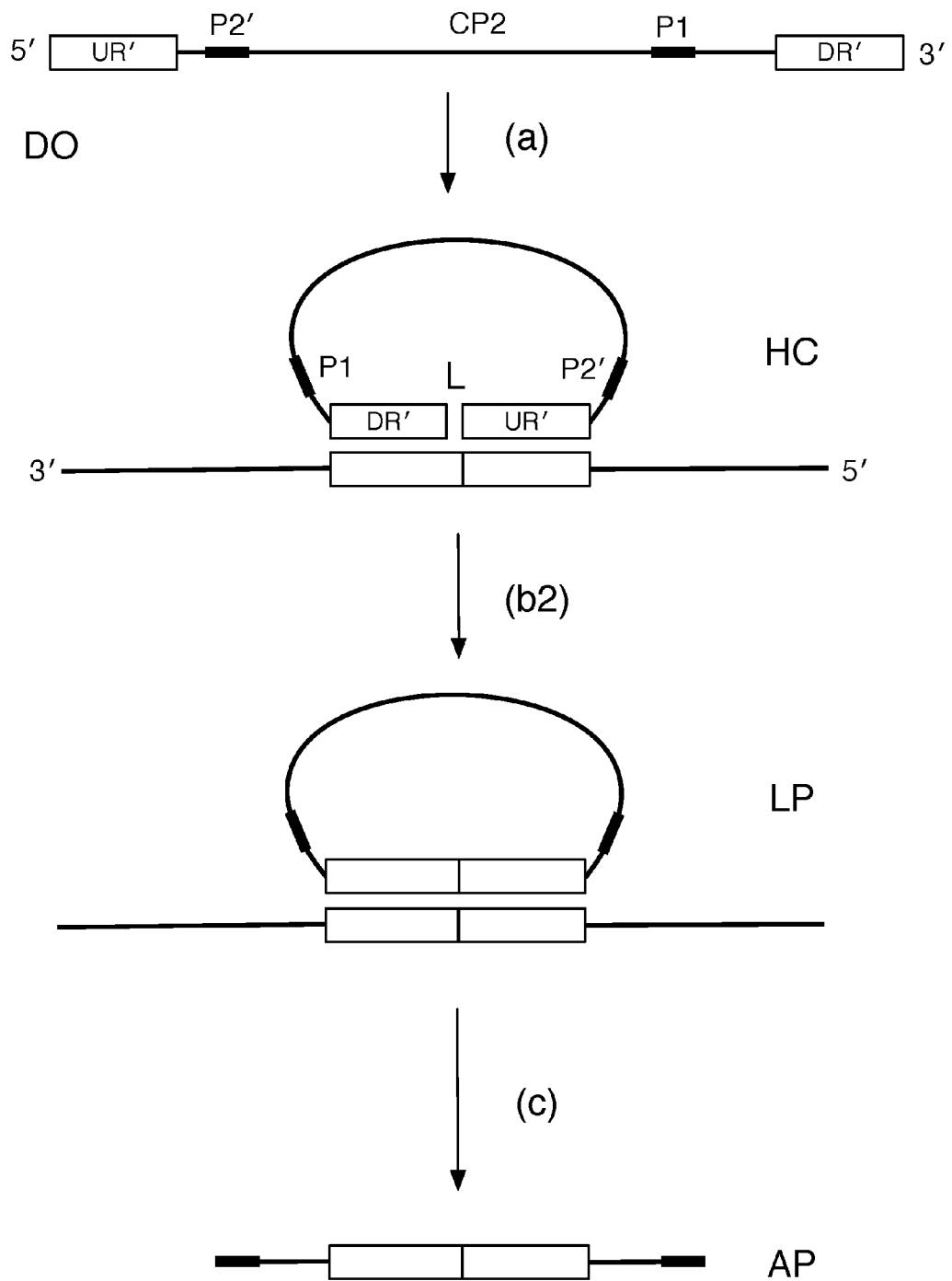

FIG. 3a depicts a circularizable assay design of the invention using a detector oligo probe (DO) that can (a) hybridize via DR' and UR' regions to a target sequence, forming a (noncovalently) circularized structure. After treatment with a nuclease and ligase, a circularized ligation product can then be (c) amplified. FIGS. 3b, 3c, and 3d illustrate partially hybridized DO detectors, detectors hybridized to non-target sequences, or nonspecifically hybridized detectors, which can be digested by nucleases or be unsuitable for exponential amplification.

Figure 4:
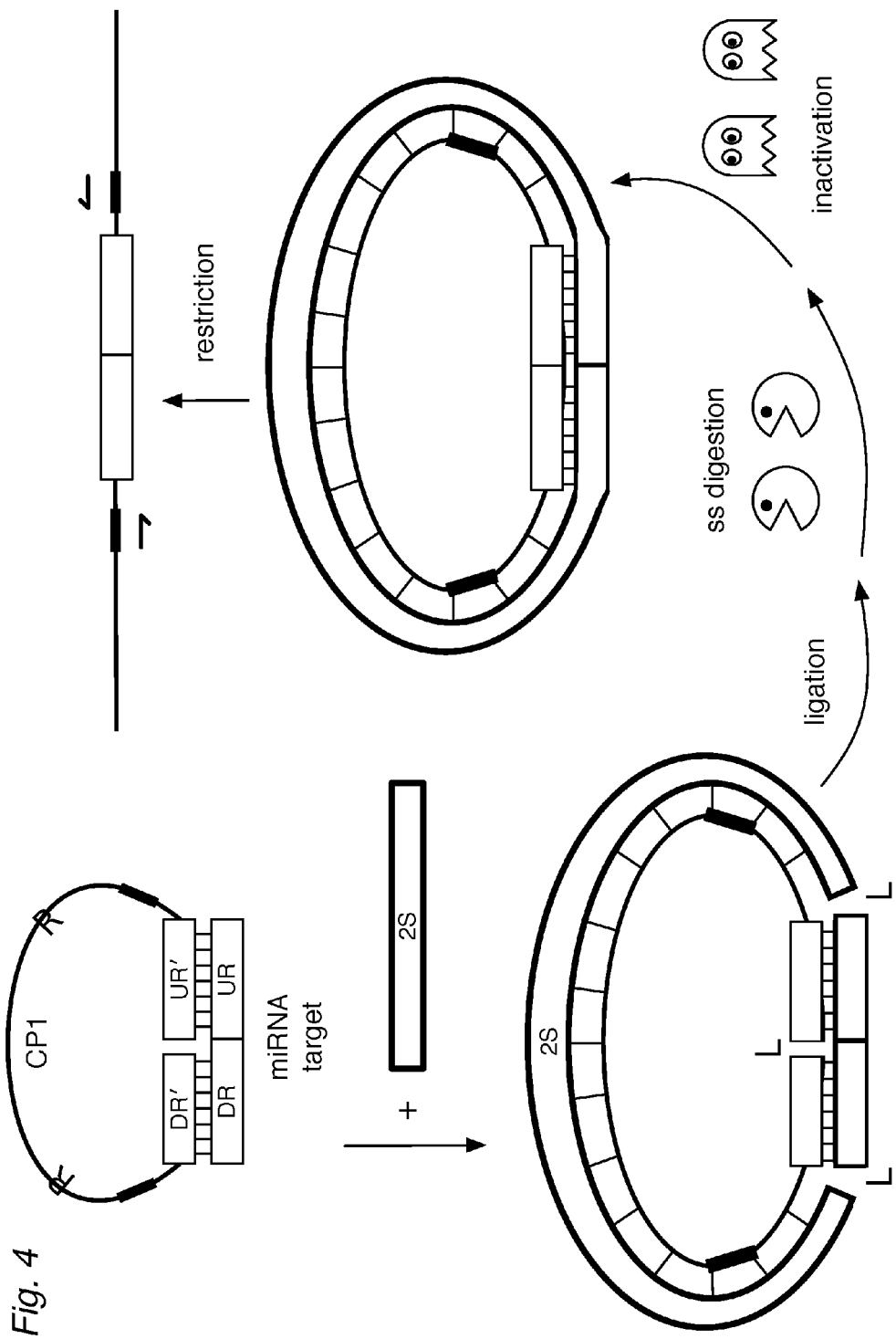

FIG. 4 shows an assay of the invention where a (universal) second strand (2S) is provided during hybridization so that the target (DR-UR), DO, and the 2S form a circularized, double-stranded structure. Treatment with ligase results in a covalently circularized ligation product. Optionally, ss-nucleases can be used to degrade excess detectors and hybridization complexes that are not specific for the target. The nucleases can be inactivated. If desired, the circularized structure can be linearized, for example by a restriction endonuclease.

Figure 5A:
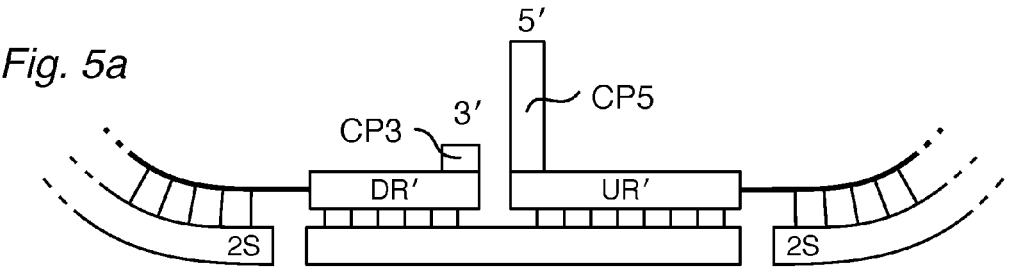
Figure 5B:
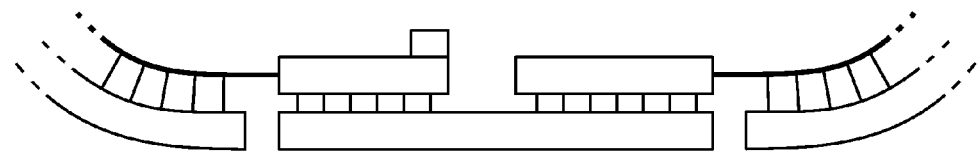
Figure 5C:
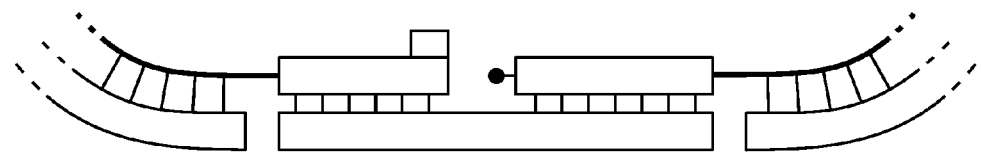
Figure 5D:
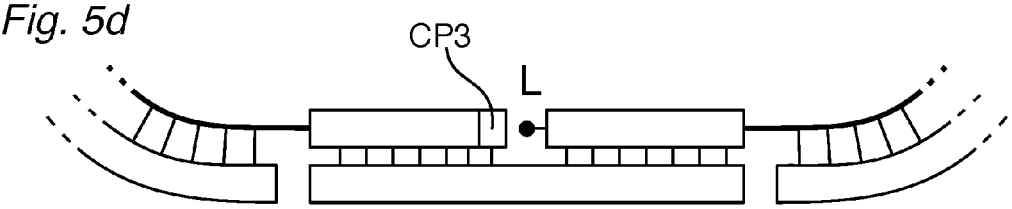

FIG. 5a shows a detailed view of a hybridization complex using a variant circularizable DO having a short noncomplementary flap (CP5) on its 5' end, and optionally a short noncomplementary sequence (CP3) on the 3' end. FIG. 5b shows the hybridization complex after the CP5 is removed by a flap nuclease, such as Fen-1. If desired, the 5' end can be phosphorylated, as in FIG. 5c. FIG. 5d illustrates how CP3 can fill in the gap left by Fen-1, so that the DO can be ligated into circularized form as in FIG. 5e. The noncomplementary CP5 and/or CP3 flaps can be incorporated in any of the DD and UD designs.

FIG. 6a provides target sequences (SEQ ID NOs: 33-56) used to design detectors for mRNA expression products for 24 human genes. The genes were selected to demonstrate detection over an expected range of 6 orders of magnitude in abundance, with 10, 1, and 0.1 ng sample RNA input. The number of amplified ligation products, confirmed by sequencing, are shown for anchored detector designs (FIGS. 6b, 6c, and 6d) and circularizable designs (FIGS. 6e, 6f, and 6g). The x-axis is for the first technical replicate; the y-axis is for the second replicate.

DETAILED DESCRIPTION OF THE INVENTION

Ligation Assays, Generally

Figure 1:
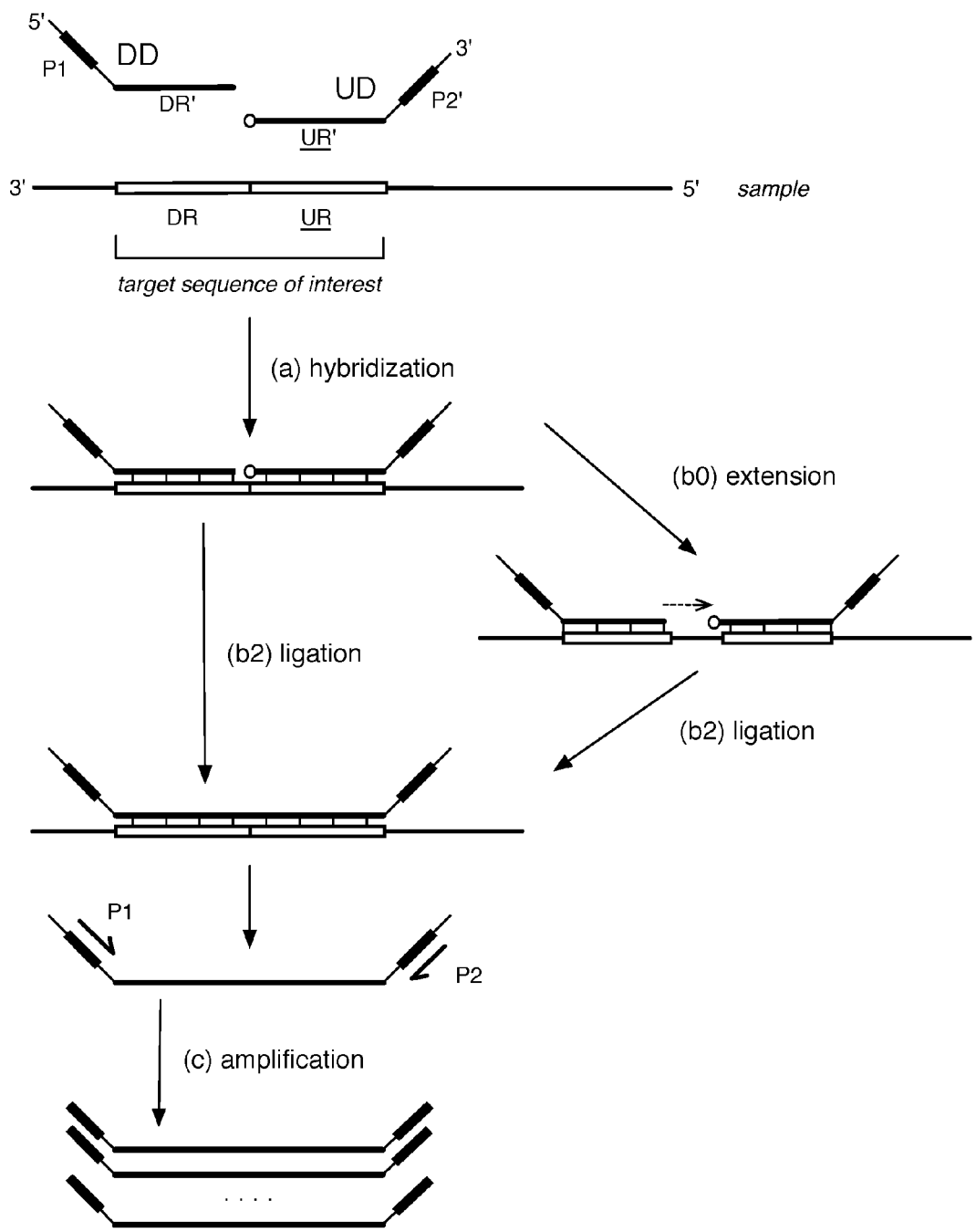
FIG. 1 illustrates a representative ligation assay for detecting target nucleic acid sequences. Briefly, downstream detector (DD) and upstream detector (UD) probe oligonucleotides are allowed to (a) hybridize to a target sequence of interest, having DR and UR regions, in a sample. For convenience of identification, upstream regions are often underlined herein. While hybridized to the DR and UR of the target sequence, the DD is (b2) ligated selectively to the UR. Optionally, the DD is (b0) extended prior to (b2) ligation. The ligation product is optionally (c) amplified via amplification regions P1 and P2' by one or more primers, such as P1 and P2.

A typical ligation assay is illustrated schematically in FIG. 1, which is discussed in more detail in Example 1. A sample that may contain target nucleic acid sequences of interest is contacted with a pool of detector oligonucleotide probes ("probes" or "detectors"). For each sequence of interest, a pair of detectors is provided: a downstream detector (DD) and an upstream detector (UD). A downstream detector can have a portion (DR') that is complementary to a region of the target sequence designated as a downstream region (DR). An upstream detector can have a portion (UR') that is complementary to a region of the target sequence designated as the upstream region (UR). Here, the terms "downstream" and "upstream" are used relative to the 5'-to-3' direction of transcription when the target sequence is an mRNA, and for convenience the regions designated as upstream are often shown underlined.

As shown in FIG. 1, the DR' of the DD and the UR' of the UD for each target sequence are allowed to hybridize to the corresponding DR and UR of the target sequence, if present in the sample. When the DR and UR of a target sequence are adjacent and the DR' and UR' of the pair of detector oligos are specifically hybridized to the target sequence to form a hybridization complex, the adjacent detectors DD and UD can be ligated. Thus, formation of a DD-UD ligation product serves as evidence that the target sequence (DR-UR) was present in the sample. In cases where the DR and UR of a target sequence are separated by at least one nucleotide, the ligation step can be preceded by (b0) extending the DR' using the sample as a template so the extended DR' and UR' become adjacent and can be ligated. The ligation product can then be detected by a variety of means; if desired, the products can be amplified prior to detection.

The present invention provides methods where hybridization complexes are exposed at one or more steps to at least one nuclease that can degrade single strands of nucleic acid. As discussed in more detail below, the invention provides detectors and other components of the assay that are configured to selectively resist the nucleases when detecting target sequences. The nucleases can degrade excess or unused detectors, or detectors that are nonspecifically or nonproductively bound to components in the sample that are not of interest. The strategic use of nucleases enables the ligation assay to be performed by adding one reagent after another in a single reaction container, starting with the sample.

Samples

The samples used in the method can be any substance where it is desired to detect whether a target sequence of a nucleic acid is present. Such substances are typically biological in origin, but can be from artificially created or environmental samples. Biological samples can be from living or dead animals, plants, yeast and other microorganisms, prokaryotes, or cell lines thereof. Particular examples of animals include human, primates, dog, rat, mouse, zebrafish, fruit flies (such as *Drosophila melanogaster*), various worms (such as *Caenorhabditis elegans*) and any other animals studied in laboratories or as animal models of disease. The samples can be in the form of whole organisms or systems, tissue samples, cell samples, or samples that are cell-free. Particular examples are cancer cells, induced pluripotent stem cells (iPSCs), primary hepatocytes, and lymphocytes and subpopulations thereof. The samples can be provided in liquid phase, such as cell-free homogenates or liquid media from tissue cultures, or nonadherent cells in suspension, tissue fragments or homogenates, or in solid phase, such as when the sample is mounted on a slide or in the form of formalin-fixed paraffin-embedded (FFPE) tissue or cells, or when cells are grown on or in a surface, as long as detectors can be put into contact for potential hybridization with the sample nucleic acids.

Nucleic Acids

The nucleic acids to be detected in samples include the genome, transcriptome, and other functional sets of nucleic acids, and subsets and fractions thereof. The nucleic acids can be DNA, such as nuclear or mitochondrial DNA, or cDNA that is reverse transcribed from RNA. The sequence of interest can also be from RNA, such as mRNA, rRNA, tRNA, siRNAs, antisense RNAs, or long noncoding RNAs. The nucleic acid can be a microRNA (miRNA) at any stage of processing, such as a primary microRNA (pri-miRNA), precursor microRNA (pre-miRNA), a hairpin-forming microRNA variant (miRNA*), or a mature miRNA. Detection of microRNAs is discussed in Example 3a.

Relatively short target nucleic acids, such as mature miRNAs, can be lengthened to enhance hybridization to the detectors. For example, many microRNAs are phosphorylated at one end, and can be lengthened by chemical or enzymatic ligation with a supplementary oligo. The supplemental oligo can be single-stranded, double-stranded, or partially double-stranded, depending on the ligation method to be used. If desired, the supplemental oligo can be unique to each target sequence, or can be generic to some or all of the target sequences being ligated. The detectors can then be designed with extended DR' and/or UR' regions that include a portion that hybridizes to the supplemental sequence. A target sequence can also be supplemented by adding nucleotides, such as by polyadenylation, where the extended detectors include at least a portion to hybridize to the supplemental polyA tail. Detection of a family of mature miRNA sequences using extended detectors is discussed in Example 3b and illustrated in FIG. 2j.

The amount of nucleic acid in the sample will vary on the type of sample, the complexity, and relative purity of the sample. Because of the sensitivity of the assay, the sample can be taken from a small number of cells, for example from fewer than 100,000, 10,000, 1000, 100, 50, 20, 10, 5, or even from a single cell. The total amount of nucleic acid in the sample can also be quite small: less than 100, 50, 20, 10, 5, 2, 1 micrograms, 500, 200, 100, 50, 20, 10, 5, 2, 1, 0.5, 0.2 or 0.1 nanogram of nucleic acid (see FIG. 6d). The copy number of a particular target sequence can be less than 100,000, 10,000, 1000, 100, 50, 20, 10, 5, or even a single copy present in the sample, particularly when coupled with representative amplification of the ligation product for detection. The amount of input nucleic acid will also vary, of course, depending on the complexity of the sample and the number of target sequences to be detected.

Detectors

Based on the particular target sequences of interest, the invention provides pools of detector oligos where a target sequence has a pair of upstream and downstream detectors (UD and DD) that correspond to DR and UR, which are typically subsequences of the entire target sequence of interest. Detectors can be provided to detect targets that contain mutations including individual single-nucleotide polymorphisms (SNPs), gene fusions, and exon-splicing variants. An individual target sequence can have more than one set of DRs and URs, which can be selected by the user to optimize the performance of the assay. Multiple sets of DRs and URs can provide multiple measurements of the same target sequence or of different portions of the target sequence, such as different exons or exon junctions, or provide measurement of a portion of sequence that is not mutated versus a portion of sequence that may harbor a mutation.

Target Sequences of Interest

The sequences of interest can be selected from any combination of sequences or subsequences in the genome or transcriptome of a species or an environment. The set can be specific for a sample type, such as a cell or tissue type. For some sample types, the number of target nucleic acid sequences of interest can range in any combination of upper and lower limits of 1, 2, 5, 10, 20, 50, 100, 200, 500, 1000, 2000, 5000, 10,000, 20,000, 23,000, 30,000, 38,000, 40,000, 50,000, or more. The number of target sequences of interest can also be expressed as a percentage of the total number of a defined set of sequences, such as the RNAs in the human transcriptome or genes in the human genome, ranging in any combination of upper and lower limits of 0.1%, 0.2%, 0.5%, 1%, 2%, 5%, 10%, 20%, 25%, 30%, 35%, 40%, 45%, 50%, 65%, 60%, 70%, 75%, 80%, 85%, 90%, 95%, and 100%. Where large sets of detector oligos are used, it can be useful to check the full sequence of each oligo for potential cross-hybridization to other oligos in the set, where, for example, one oligo may inadvertently serve as an template to other detectors. While such non-specific artifacts can be identified by sequence, and are typically discarded from detection results, they may represent noninformative hybridization events that compete for reaction resources.

The detector oligos themselves can be DNA, RNA, or a mixture or hybrid of both. If desired, they can have a modified nucleotide such as dideoxy nucleotides, deoxyUridine (dU), 5-methylCytosine (5mC), 5-hydroxymethylCytosine (5hmC), 5-formylCytosine (5fC), 5-carboxylCytosine (5caC), and Inosine. Yet other modifications to detector oligos include modified bases such as 2,6-diaminopurine, 2-aminopurine, 2-fluro bases, 5-bromoUracil, or 5-nitroindole. Other detector oligos can have a modified sugar-phosphate backbone at one or more positions. Such modifications include a 3'-3' or 5'-5' linkage inversion, a locked nucleic acid (LNA), or a peptide nucleic acid (PNA) backbone. LNAs can be useful for their stronger hybridization properties to complementary bases, enhancing the selectivity or the overall binding affinity for the detector oligo as a whole. The modified bases or bonds can also be used at positions 1, 2, or 3 away from the point of ligation.

As shown schematically in FIG. 1, a downstream detector (DD) has a complementary downstream region (DR'), which can be at least 4, 6, 8, 10, 12, 14, 16, 18, 20, 22, 24, 26, 28, 30, 35, 40, 45, or 50 nucleotides in length. Similarly, an upstream detector (UD) has a complementary upstream region (UR'), which can be at least 4, 6, 8, 10, 12, 14, 16, 18, 20, 22, 24, 26, 28, 30, 35, 40, 45, or 50 nucleotides in length. In a given pair of DD and UD for a target sequence, the DR' and UR' need not be exactly the same length, but will typically be similar so they can hybridize to the target under similar conditions and stringency.

As discussed in more detail below, the detectors can be optimized for ligation, such as by providing a 5'-phosphate on the UD, although this is not necessary, depending on the selection of ligase or other ligation methods. Ribonucleotides can also be substituted at the ligatable ends of the DD and UD to increase the specificity and efficiency of ligation, as when an RNA ligase is used.

Detector Labels

Where the ligation assay proceeds directly to a detection step, either or both detectors can be designed to be labeled appropriately for detection. For example, the detector can be labeled with a color or fluorescent dye, latex bead, quantum dots, or nanodots. The label can also take the form of an additional nucleotide sequence that serves to enable detection and identification, such as a barcode sequence. For example, a useful barcode sequence can uniquely identify the specific gene or target sequence, or a group of select genes or target sequences within the sample that are being measured. Such sequences can be positioned between the UR' and P2' sequence, and/or between the DR' and P1 sequence, so they are amplified when using flanking primers. This sequence can also be a random sequence, useful for identifying the number of copies of the target gene in the sample, independent of the particular efficiency of any amplification step.

Hybridization

Returning to the steps of the assay, the detectors are provided so that they contact the sample to allow the detectors to hybridize specifically to the target nucleic acids. Optionally, the conditions for hybridization can be adjusted or fine-tuned to permit other steps to be performed in the same environment. For example, the same buffers used for hybridization can be used for lysing cells in a sample, promoting hybridization of certain cell types, facilitating removal or permeation of cell walls, cell membranes, or subcellular fractions, as desired. Depending on the ligation method used in the assay, hybridization conditions can be selected to be compatible with conditions for ligation as is, or with the addition of one or more components and preferably without requiring a change of the reaction container when transitioning from hybridization to ligation steps.

Ligation

The ligation reaction can occur by chemical ligation or by using a ligase enzyme or a ligation-facilitating co-factor. A variety of nick-repairing ligases are commercially available to catalyze the formation of a phosphodiester bond between adjacent single-stranded polynucleotides when hybridized to another single-stranded template, such as to join DNA to RNA when hybridized to template. An example is bacteriophage T4 DNA ligase, which is generally understood to use ATP as a co-factor. The ATP can be supplied during the ligase reaction. In other reactions, the ligase can be pre-adenylated. In yet other reactions, the UD must be pre-adenylated at the 5' end, as with a 5' App DNA/RNA ligase. The UD in a typical reaction will have a 5'-phosphate to facilitate ligation to the DD, although this is not necessary, depending on the selection of ligase and ligation conditions. (Where a 5'-phosphate on the DD is required for efficient ligation, using a comparable oligonucleotide without 5'-phosphorylation can be used to inhibit or reduce undesired ligation.) Preferred ligation conditions include 10, 25, 50, 100 mM Tris-HCl (pH 7.5, 8.0, or 8.5); at least 10 mM, 5 mM, 2 mM, 1 mM $MgCl_2$; at least 2 mM, 1 mM, 0.7 mM, 0.5 mM, 0.2 mM, 0.1 mM, 0.05 mM ATP; or at least 10 mM, 7 mM, 5 mM, 2 mM, 1 mM, 0.5 mM DTT or other antioxidant. T3 DNA ligase can also be used, which can ligate a broader range of substrates and has a wider tolerance for salt concentration.

As discussed above, the ligation step can be preceded by an optional extension step, as in FIG. 1, step (b0). The ligation step can also be preceded by an optional cleavage step, such as by a nuclease, to remove any overhangs. In other cases, a portion of the DD can overlap with the UR sequence to which the UD hybridizes, so that after hybridization of the UD and the DD, there is an overhang sequence of 1, 2, 3, or more bases. A useful enzyme for removing an overhang is a Flap endonuclease, such as Fen-1.

Amplification

If desired, the ligation product can be amplified (for example by PCR or qPCR) to facilitate detection. Amplification methods and instruments are commercially available, including PCR plate and droplet formats, and the amplification enzymes (such as Taq and its commerical variants) and reaction conditions can be selected and tailored to the particular platform. Optionally, the polymerase selected for amplification can have strand-displacing activity. As illustrated in FIG. 1, the detectors can have additional sequences ("tails") including primer hybridization sequences (e.g. P1, P2') or complements thereof, that serve as amplification sequences, so that after ligation, the ligation product can be amplified with a pair of amplification primers (P1, P2). An exemplary downstream amplification sequence (P1) is (SEQ ID NO: 1)
5'-CAAGCAGAAGACGGCATACGAG-3', which can be used with a primer having the same sequence (P1). An exemplary upstream amplification sequence (P2') is (SEQ ID NO: 2)
5'-ATCTCGGTGGTCGCCGTATCATT-3', which can be used with primer P2 (shown in 3'-to-5' orientation):

(SEQ ID NO: 3)
3'-TAGAGCCACCAGCGGCATAGTAA-5'.

If desired, the amplification primer can incorporate a barcode sequence, for example a barcode sequence that uniquely identifies the sample in a multi-sample experiment, and optionally has redundant and/or error-correction features. In some experiments, for example, different sample barcodes can be used for 96, 384, 1536, or more generally $2^n$ or $4^n$ different samples that are prepared with different barcodes separately for some steps, such as hybridization, ligation, and amplification, and combined for others, such as detection. The barcode sequence can be incorporated into the primer, such as 3' to the amplification sequence, so that the barcode becomes part of the amplified strand. In other instances, the amplification sequence of the primer can be extended by an additional sequence to provide a primer hybridization sequence that can be used for use in subsequent sequencing steps. The barcode may also be interposed between the amplification sequence, and if desired, the extended amplification sequence, and another sequence that can be used for capture, such as capture onto a surface as part of a sequencing process, and/or for yet another primer hybridization sequence that is used for sequencing. In each case the barcode will be amplified with the rest of the detector sequences, for instance forming a single amplified, elongated molecule that contains sequencing primer hybridization sequences, sample barcode, and a gene-specific sequence, which may include a gene-specific barcode or a target molecule-specific barcode as well as sequence or complement to the sequence of the target gene. In the case where the targeted oligo is a cDNA, a gene-specific sequence or a sample-specific sequence can be added as part of the primer used for reverse transcription, and be a part of the sequence targeted by the UD and DD.

In other instances, methods known in the art can be used to amplify the ligated DD and UD sequences, such as by repetitive cycles of (1) ligation, (2) heating to melt off the ligated product, (3) cooling to permit hybridization of DD and UD to the target, (4) ligation, then repeating the heating (2), cooling (3), and ligation (4) steps. These additional amplification steps can be performed before amplification step (c), during which the sample barcodes and other sequences are added to the ligated UD and DD sequence. The target of the UD and DD hybridization may also be amplified by whole transcriptome amplification of RNA or amplification of cDNA.

Detection

The ligation product (or its amplicons) can optionally be detected by methods such as sequencing, qPCR, or labeling for detection on an array or other molecule detection. Other detection methods include flow-through systems for counting labeled molecules. Depending on the detection method, the skilled user will be able to modify the design of the detectors and amplification primers to include functional features that are appropriate, such as for bridge amplification on a sequencing flow cell. The experimental resources used for amplification and detection can be limited and are often among the most expensive, and their consumption can be optimized by reducing the number of non-informative assay components present at various stages of the assay.

Nucleases

Accordingly, the invention provides nucleases and assay components that are configured to resist degradation to enable more efficient use of resources and more sensitive detection. As a further advantage, the invention enables a simpler assay workflow that can be performed in a single reaction container or entirely in liquid phase.

The nuclease can be an enzyme that digests or degrades single strands of nucleic acids. Preferably the nuclease does not digest (or has significantly less activity on) double strands, including DNA:RNA hybrids. For example, the nuclease can have less than 10%, 5%, 2%, 1%, 0.5%, 0.2%, or 0.1% the activity on double strands compared to single-strands on a molar substrate ratio under the same conditions. Similarly, the nuclease can be selected so it does not appreciably digest at single-stranded nicks in a double-strand. The nuclease can be an endonuclease that degrades single strands, such as mung bean nuclease under certain conditions. The nuclease can also be an exonuclease that degrades single strands, which can be single strands of DNA. For example, a nuclease having single-stranded 3'-to-5' exonuclease (3' exo) activity includes Exonuclease I from *E. coli* (exo I) and T3 exonuclease. Enzymes such as exonuclease T (RNase T), which has 3' exo activity on DNA and RNA single strands, can be used as long as the detectors have been ligated and the RNA strands are no longer needed in the assay. Nucleases having single-stranded 5'-to-3' exonuclease activity include exonuclease VIII and RecJ$_f$. The nuclease can be an enzyme that digests 5' overhangs or flaps, such as Flap endonuclease 1. Nucleases can be used singly or in a cocktail of nucleases, such as a pair of 3' and 5' exonucleases.

The nucleases can be used at various stages of the assay. For example, a nuclease can be provided (b2) after the ligation step (b1) to remove unligated or excess detectors, as in FIG. 2e. The nuclease can also degrade detectors that are only partially or nonspecifically hybridized to target sequences, as in FIG. 2f. If compatible with the ligation conditions used, the nuclease can also be provided during the ligation step (b1 and b2 together), or even before the ligation step (b2, then b1) as long as it does not interfere with the intended detection of target sequences. Depending on the assay design, the nuclease can be provided before, during, or after the optional (b0) extension and (d) amplification steps, or at multiple steps to effect the desired purpose of removing undesired target, detectors, other oligos, or any products.

When the nuclease activity is no longer desired, the nucleases can be removed or inactivated, such as after the ligation step. Nucleases can be inactivated by methods selected for a particular nuclease but will not substantially interfere with the rest of the assay. For some nucleases, a nuclease inhibitor (as in FIG. 4, lower right) or chelating agent, such as EDTA, can be added as long as it does not interfere with (or can be removed prior to) a subsequent step that may require Mg$^{++}$ for example. Other nucleases can be inactivated by heat, for example single or repeated incubation at 70° C., 75° C., 80° C., 85° C., 90° C., 95° C. or 98° C., for 1, 2, 5, 10, 15, 20, 25, 30, 45 minutes, or 1 hour. To resist the activity of nucleases provided at one or more steps of the invention, components of the assay are provided by the invention in various configurations that permit detection of target sequences. Selection of the configuration method will depend, of course, on the particular nuclease being used.

Anchored Detectors

In one configuration, the upstream detector has a second region (UR2') that is complementary to a second region of the target sequence (UR2), as illustrated in FIG. 2a. Because the tail of the UD can hybridize to a separate portion of the target, this configuration can be described as an "anchored" detector, as in FIG. 2b. The anchor at the 3' end of the UD hybridizes with the target to form a double-strand and is thus configured to resist digestion to nucleases that degrade single strands, such as 3' exonucleases like exo I.

As a separate target-binding region, the anchor UR2' can be used to provide additional discrimination between similar sequences, such as isoforms of a family of genes where sequence differences between isoforms are found beyond the range of the DR and UR target sequence.

The UR2' can be at least 4, 6, 8, 10, 12, 14, 16, 18, 20, 22, 24, 26, 28, 30, 35, 40, 45, or 50 nucleotides in length. The UR2' can be separated from the UR' by a noncomplementary region (CP1), which can be at least 8, 10, 12, 14, 16, 18, 20, 22, 24, 26, 28, 30, 35, 40, 45, 50, 60, 70, 80, 90, or 100 nucleotides in length. In general, the UR2' will be upstream relative to the UR'. If an amplification region (such as P2') is present, it can be upstream of the UR', such as within the CP1 or part of UR2' to allow amplification of the UR' portion as shown in FIG. 2c to generate the amplification products (AP) in FIG. 2d.

In a mirror-image configuration, it is the downstream detector that has the anchor region (DR2') complementary to a second region of the target sequence. The DR2' anchor hybridizes to a DR2 on the target so that the configuration resists the action of 5' ss-exonucleases. The DR2' of the DD will generally be downstream relative to the DR'. If an amplification region (such as P1) is present, it can be downstream of the DR' to allow amplification of the DR' after ligation. Anchored DDs and UDs can be used separately or in combination to resist a cocktail of nucleases.

Because the separate anchor region of the detector can affect the hybridization characteristics of the detector via monomolecular kinetics, the compositions and relative lengths of the DR2', CP1(s), DR', UR' and UR2' can be tuned to optimize target selectivity between the detector pair and among the pairs of the detector pool.

Detectors that are not used in the ligation reaction can be degraded as shown in FIG. 2e. Moreover, incompletely bound detectors, such as those in FIG. 2f, can also be degraded, for example when the UR' of a UD binds to the UR of a target, but the UR2' does not bind, whether because the UR' is bound to a non-target sequence or to a target that was related to the intended target UR but lacked a UR2. Similarly, an anchored DD that binds a DR2 but not the DR of a target will be susceptible to a 3' ss-exonuclease (or will not generate a valid ligation product with a corresponding UD). Other detectors will fail to be amplified, for example detectors in excess of target sequence in the sample or detectors that are bound nonspecifically to nontarget sequences. The use of anchored detectors can therefore increase the specificity of the ligation assay for target sequences while allowing nucleases to degrade excess or unused detectors.

Blocked Detectors

Another configuration has detectors that are nuclease-resistant by having a nuclease-blocking group at one end. FIG. 2h shows a DD, having a 5'-blocking group, that can be used in combination with a 5' exonuclease. Also shown is a UD having a 3'-blocking group for use with a 3' exonuclease. Preferably when a 5' or 3' exonuclease is used where there are multiple targets and pairs of detectors, all of the downstream or upstream detectors have a 5' or 3' block, respectively.

Useful configurations for resisting nucleases include termination with an inverted nucleotide such as deoxythymidine (idT), a dideoxynucleotide such as dideoxythymidine (ddT or iddT), or 2'/3'-O-acetyation of the terminal nucleotide. Depending on the substrate preferences of the nuclease selected, one of the other modified nucleotides described earlier can be used as a blocking group. Alternatively, one or more of the terminal nucleotides are attached to the rest of the oligo via one or more phosphorothioate bonds instead of naturally occurring phosphodiester bonds. Other modifications that may resist a nuclease include the LNA or PNA backbones discussed earlier. It can be useful to combine any of the preceding features in a single detector or both detectors to resist the action of the nuclease selected.

Protectors

Yet another configuration provides one or more oligos that protect the detectors by hybridizing to the DD or UD at a region that will not interfere with hybridization of the DR' or UR' regions complementary to the target sequence. For example in FIG. 2i, a DR2 protector oligo is provided to hybridize to a DR2' region at the 5' end of the DD, forming a double-stranded configuration (indicated by a brace) that is resistant to 5' exonucleases. If a 3' exonuclease is to be used, then a UR2 protector can be provided to form a double-strand at the 3' end of the UD. The protector oligos can themselves be protected from exonuclease activity by a blocking group or bond as described above. For example, a 3'-blocked UR2 protector is shown in FIG. 2i, and a 5'-blocked DR2 protector is shown in FIG. 2j. If a cocktail of 5' and 3' exonucleases is to be used, then both DR2 and UR2 protectors can be provided, optionally with 5'- or 3'-blocking groups, respectively.

Circularizable Detectors

In a circularizable configuration, the upstream complementary region (UR') and downstream complementary region (DR') are on a single detector oligo (DO), as shown in FIG. 3a. The DO can have in the 5'-to-3' direction: (B) an upstream complementary region (UR'); (C) an optional amplification region (P2'); (D) a noncomplementary region (CP2) having a sequence that is not complementary to the target sequence; (F) a downstream complementary region (DR'); and (E) an optional amplification region (P1). The DO can be at least 50, 60, 70, 80, 90, 100, 110, 120, 130, 140, 150, 200 bases in length to allow the molecule flexibility to circularize.

In the presence of a target sequence DR-UR, the detector can (a) circularize on the target, forming a hybridization complex (HC) that is resistant to single-stranded exonucleases and that can be (b2) ligated. If the amplification regions are provided in the appropriate orientation, the ligation product (LP) can be (c) amplified with P1 and P2 primers to form amplification product (AP) that contains the joined DR' and UR' regions.

The DOs that are not specifically hybridized to the target or are bound incompletely to the target are susceptible to degradation by nucleases (FIG. 3d) or the P1 and P2' amplification regions will not be in the correct orientations for primer amplification, as illustrated in FIG. 3b or 3c. In some instances, the detector may be amplified, but it will be amplified linearly, rather than exponentially. In such cases, the minor sequences can be detected and discounted or removed from the detection results computationally.

Second Single-Strand (2S)

Still another configuration provides a single-stranded DNA oligonucleotide (2S) to hybridize to the single-stranded portion of the detector to form a double-stranded hybridization complex, as illustrated in FIG. 4. The 2S oligo can be complementary to the CP1 so that the entire structure becomes double-stranded. Where the assay is intended to detect multiple target sequences, the same 2S can be used generically to form the circular structure since it does not rely on hybridization to target sequences. The structure can then be ligated, completing the circular, double-stranded structure and resistant to exonucleases, ss-endonucleases, and nick-endonucleases.

Optionally, the circular structure can be deliberately nicked or cut, for example by a nicking endonuclease. The DO can have a restriction endonuclease recognition site so the circular structure can be linearized if desired. To avoid digesting target sequences or detectors, the recognition site selected for CP1 can be a relatively rare site such as for AscI, FseI, AsiSI. If desired, linearized structures can be separated from circular structures by conventional methods.

Flaps

Figure 5E:
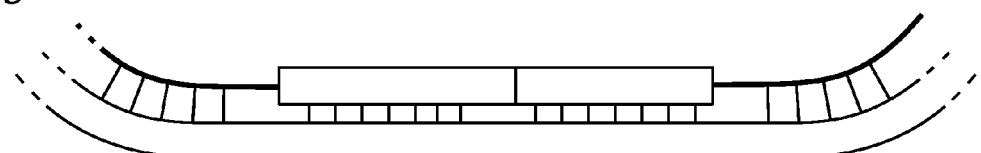

The circularizable DO can be configured so that it has a (A) a noncomplementary region (CP5) in the 5' direction of the UR' and (G) an optional noncomplementary region (CP3) in the 3' direction of the DR', as shown in FIG. 5a and discussed in Example 4. A second strand can be provided that has, in the 5'-to-3' direction: P2, CP2', P1' so that, together, the target nucleic acid, a detector oligo, and the second strand form a hybridization complex having a 5' flap. A nuclease, such as Fen-1 can be used to remove the 5' flap (FIG. 5b). The 5' end of the circularizable detector can be phosphorylated (FIG. 5c). If desired, the optional CP3 region can then hybridize to target sequence, forming a 3' terminus that can be ligated (FIG. 5d) to the adjacent UR' to form a ligated product (FIG. 5e).

Steps in Solid, Liquid Phases

In some embodiments, the hybridization, ligation, or extension steps can be performed while the target sequence is in situ. This can be particularly useful, for example, when the sample is on a histological slide, so that the ligation is known to occur at a recordable location and can be compared to similar reactions at other locations on the slide. In a particular embodiment, the ligation products can be eluted from the sample in situ for collection and further processing, preferably eluting from small areas to preserve the location information and morphological context of the ligation reaction products.

In other embodiments, one or more of the steps can be performed in liquid phase, such as in a microfluidic system, so that one or more of the steps does not involve capture to a solid phase, such as to a bead or a plate surface. For example, any one or combination of the hybridization, extension, ligation, nuclease digestion, amplification, or detection steps can be performed in liquid phase. In a mixed phase assay, a solid phase can be used to immobilize one or more of the sample, the detector oligos, the hybridization complex, the extension product, the ligation product, or the amplification product. In particular, the target nucleic acid can be attached to a solid surface during the hybridization step, the ligation step, or both. The mixed phase format allows the components to be transferred from one reaction environment to another, or the conditions to be changed as the components remain in one container.

Adding Successively to the Same Reaction Container

Alternatively, the reactions can be optimized so that at least one of steps is performed by adding reagent, such as an enzyme or buffer component, successively, so that a reaction takes place in the same container as the preceding step, optionally without requiring an intervening wash or transfer step. Preferably, the sequence of additions does not require significant additions of liquid volumes to dilute the components for the next reaction, for example no more than 1-, 1.5-, 2-, 2.5-, 3-, 5-, 10-, 15-, or 20-fold dilution between the initial sample and preparation for detection. The components to be added can be provided in a kit, as described below.

Attenuators

In cases where there is more than one target sequence of interest in a given sample, it is likely that they will be present in different amounts. Moreover, the amount of a target sequence can vary among similar samples. Ideally, a detection assay will have sufficient dynamic range to measure the presence of the different target sequences quantitatively in a single experiment. For some types of samples, however, the range of abundance for various sequences of interest can span several orders of magnitude. For example, when profiling the RNA expression products of a cell, individual sequences of particular interest may be present in very few copies, while others are highly abundant target sequences (HATs). The HATs can be present in a sample in such large numbers that they may diminish the ability of a method to detect the presence of less abundant target sequences.

Depending on the cell or tissue type, such highly abundant HATs can include sequences encoding what are generally referred to as housekeeping genes. Examples of HATs include sequences that encode all or a portion of myoglobins, actins, tubulins, ubiquitins, heat-shock proteins (HSPs), ribosomal proteins, ribosomal RNAs (rRNAs), micro-RNAs (miRNAs), or small nuclear RNAs (snRNAs). Other examples of HATs can encode all or a portion of cytochrome c, glyceraldehyde 3-phosphate dehydrogenase (GAPDH), ribosomal protein L7 (RPL7), ribosomal protein S6 (rpS6), snRNA RNUs, phosphoglycerokinase (PGK), tyrosine 3-monooxygenase/tryptophan 5-moonoxygenase activation protein zeta (YWHAZ), β-actin, or β-tubulin. Further examples include sequences encoding all or a portion of α-2-microglobulin, vimentin, and fibronectins. Yet other examples of HATs encode all or part of a cytochrome such as mitochondrially encoded cytochrome b (MT-CYB), outer mitochondrial membrane cytochrome b5 type B, microsomal cytochrome b5 type A (ACYB5A), and ascorbate-dependent cytochrome b3 (CYBASC3). Because which sequences are highly abundant can differ from one sample type to another, such as between different tissues or cell types, certain target sequences can be designated as a predetermined set of potential HATs based on a search of the literature for that type of sample, or can be determined by performing preliminary assays to determine the more abundant sequences in the sample type. Various attenuator oligonucleotides ("attenuators") can be used to attenuate the overall number of HAT-related ligation products to be detected. Some attenuators are provided that can to provide positive detection of the HAT in the sample, but at a lower level of signal.

An attenuator useful in the invention is shown in FIG. 2g, where a UR2' oligo is provided to hybridize to UR2 targets in competition with detectors. Similarly, UR2, DR2', and DR2 oligos can be provided to compete with the binding of portions of anchored detectors to HATs, thereby attenuating the total number of detectors that form HAT-related ligation products. Particularly useful attenuators can have a portion of DR2 and a portion of DR; or have a portion of UR and a portion of UR2, thereby competing for two portions of the same anchored detector.

For circularizable detector designs, an attenuator can be an oligonucleotide that has a portion that is identical or complementary to UR or DR, or both. Attenuators can also take the form of oligos that fill a gap, such as shown in FIG. 5b, but are blocked from yielding a ligatable product.

Cleavable Detectors

It can be desirable for a detector oligo to contain one or other modifications that can be selectively cleaved by treatment after the ligation or optional amplification step. For example, a detector oligo can have a dU located so that it will not interfere with hybridization or ligation steps. After ligation, however, products incorporating the dU oligo can then be cleaved by dU-specific enzymes, such as uracil-DNA glycosylase followed by endonuclease VIII. Another selectively cleavable site can be a restriction enzyme cleavage site that is not present in the target sequences of interest to be detected.

Kits

The invention provides kits for performing the methods described above, comprising detector oligos, and optionally a nuclease, a ligase, and/or a polymerase. The kits can further provide reaction buffers for the enzymes in the kit or buffer components to be added to reactions suitable for the enzymes. The component can be suitable for addition to a container for an enzyme reaction to prepare a suitable reaction buffer for the enzyme. The component can also be selected to be compatible with the reaction buffer for the preceding step of the method so that the component can be added to the same container to form a reaction buffer for the next enzyme to be used. Thus, the components can be selected to enable an "add-add-add" strategy for multiple steps of the assay to minimize transfers of sample, oligos, enzymes and/or solutions between separate containers.

The kits can also have eluent solutions suitable for removing oligonucleotides, such as ligated oligonucleotides, from a tissue sample for further analysis. The kits can further have amplification primers suitable for use with the detectors of the kit.

EXAMPLES

Example 1: Representative Ligation Assay

A representative method is provided to illustrate ligation assays. Here, over 100 RNA expression products were detected in a sample of cells using a multiplex assay format. For each expression product, the assay was designed to detect one or more sequences of interest within the full sequence of the product. For example, in human cells, a GAPDH gene encodes the enzyme glyceraldehyde 3-phosphate dehydrogenase; three different sequences of interest within the RNA transcript of the GAPDH gene were independently detected as target sequences. One such RNA sequence, identified here as GAPDH_2, was
5'-CGACCACUUUGUCAAGCUCAUUUCC UGGUAUGACAACGAAUUUGGCUACA-3' (SEQ ID NO:4)
where a 5' end was designated "upstream" (underlined) and the 3' end was designated "downstream" for the direction of transcription and translation. The same GAPDH_2 sequence can be shown in the 3'-to-5' direction for later convenience of discussion:

```
                                          (SEQ ID NO: 5)
3'-ACAUCGGUUUAAGCAACAGUAUGGUCCUUUACUCGAACUGUU
UCACCAGC-5'
```

A downstream region (DR) was defined as the downstream 25 bases of GAPDH_2:

```
                                          (SEQ ID NO: 6)
             3'-ACAUCGGUUUAAGCAACAGUAUGGU-5'
``` which has a complementary DNA sequence of DR':

```
                                          (SEQ ID NO: 7)
             5'-TGTAGCCAAATTCGTTGTCATACCA-3'
```

The upstream region (UR) was defined as the upstream 25 bases of GAPDH_2:

```
                                          (SEQ ID NO: 8)
             3'-CCUUUACUCGAACUGUUUCACCAGC-5'
``` which has a complementary DNA sequence of UR':

```
                                          (SEQ ID NO: 9)
             5'-GGAAATGAGCTTGACAAAGTGGTCG-3'
```

For GAPDH_2, a pair of detectors was designed: a downstream detector (DD) having the DR' sequence, and an upstream detector (UD) having the UR' sequence. Similar pairs were designed for each of the target sequences of interest to provide a pool of detectors for the assay. In this example, all the upstream detectors were phosphorylated at the 5' end.

In this particular example, an amplification step was to be performed later in the experiment using two primers, P1 and P2, so all UDs in the experiment included a primer sequence (P1) and all URs included a complementary primer sequence (P2'). Because amplification is not necessary to the practice of the invention, however, the sequence of the specific primers and primer sequences is a matter of selection to suit the particular amplification method, if used.

At least 10 ng of RNA isolated from human kidney or liver cell lines was placed in a well of a microtiter plate for each assay experiment. To each well was added 20 µL of 2× Binding Cocktail, which contained 5 nM of each detector (providing a final input of 0.1 pmoles per oligo), 100 nM biotinylated oligo(dT)$_{25}$, and 5 µL streptavidin-coated magnetic beads in a Wash Buffer (40 mM Tris-Cl pH 7.6, 1 M NaCl, 2 mM EDTA disodium, 0.2% SDS).

The plate was heated for 10 min at 65° C. to denature the RNA, then the temperature was ramped down over 40 min to 45° C. to allow the detectors to anneal to the target sequences in the RNA sample. The plate was then transferred to a magnetic base to immobilize the beads, allowing the supernatant, containing unbound and excess detectors, to be aspirated from the wells. The beads were washed at least three times with 50 µL Wash Buffer.

To each well was added 5 Weiss units of T4 DNA ligase in 20 µL of 1× ligation buffer, as provided by the supplier. After the beads were resuspended by pipette, the plates were incubated for 60 min at 37° C. to allow target-dependent ligation of DDs to UDs as appropriate. After the ligation reaction, the beads were immobilized and washed twice with 50 µL Wash Buffer. To release the ligated detectors from their RNA targets, the beads were resuspended in 30 µL and incubated for 5 min at 65° C. After incubation, the beads were immobilized, and the supernatant was removed and transferred to a storage plate.

For the optional amplification step, 5 µL of the supernatant, containing the ligation products, was transferred to a well of a PCR plate. Then 10 µL of a PCR cocktail was added, containing 0.45 U Taq polymerase, 0.6 µM P1 primer, 0.6 µM P2 primer, 1.5 mM MgCl$_2$, and 200 µM dNTPs. The thermocycler used the following program: 10 min at 94° C., followed by 20 to 25 cycles of 30 sec at 94° C., 30 sec at 58° C., and 30 sec at 72° C. The amplification products were then sequenced according to manufacturer's instructions. This representative ligation assay can be modified as in the following examples.

Example 2: Anchored and Circularizable Detector Designs

Upstream and downstream detector probe oligonucleotides were prepared as in FIGS. 2a and 3a for 24 target sequences identified as breast cancer targets: ACTB_1, TFF1_1, GATA3_3, GAPDH_3, CDH1_1, KRT19_2, TIMP1_2, NFKBIA_1, ESR1_1, VEGFA_3, LAMP1_2, MUC1_3, BAD_3, PTEN_1, BRCA2_1, BCAT2_3, ICAM1_2, IGF2_3, BRCA1_2, EGFR_1, BMP4_1, KIT_3, WNT1_1, and EGF_3 (in descending order of expected counts). The targets were selected for a range of expression covering 6 orders of magnitude from ACTB_1 to EGF_3. The target sequences used for the DRs and URs are shown in FIG. 6a.

The assay was performed in triplicate with 100, 10, 1, and 0.1 and 0 (control) nanograms of MCF7 total RNA as sample. The detectors were added to the sample in a volume of 1 or 2 µL and allowed to hybridize by incubating at 65° C. for 10 minutes, ramping down over 20 minutes from 65° to 45° C., then held for 20 minutes at 45° C. Exonuclease I (*E. coli*) was added to the hybridization mixture in 6 µL of 0.5 Units and incubated for 1 hour at 37° C. T4 ligase was added to the mixture in 6 µL of 5 Units and incubated for 1 hour at 37° C. A heat step was performed for 30 minutes at 80° C. The mixture was amplified by adding 2×PCR master mix. The amplification products corresponding to the target sequences were detected and quantificated by qPCR and sequencing. The results are provided in FIGS. 6b-6g.

Example 3a: Circularizable Detector Design for MicroRNAs

Circularizable DO detectors were designed for the Let-7 family of miRNAs. These miRNAs are initially transcribed as relatively long transcripts (pri-miRNAs), but are processed into pre-miRNAs, and subsequently processed into a relatively short mature form. In mature form, the highly homologous Let-7 family is shown 5'-to-3', with variants from the let-7a sequence bolded).

```
Hsa let-7a
                                     SEQ ID NO: 10
ugagguaguagguuguauaguu Hsa let-7b
                                     SEQ ID NO: 11
ugagguaguagguugugugguu Hsa let-7c
                                     SEQ ID NO: 12
ugagguaguagguuguaugguu Hsa let-7d
                                     SEQ ID NO: 13
agagguaguagguugcauaguu Hsa let-7e
                                     SEQ ID NO: 14
ugagguaggagguuguauaguu Hsa let-7f
                                     SEQ ID NO: 15
ugagguaguagauuguauaguu Hsa let-7g
                                     SEQ ID NO: 16
ugagguaguaguuuguacaguu Hsa let-7h
                                     SEQ ID NO: 17
ugagguaguaguuugugcuguu
```

Using Hsa let-7a as an example, the DR' was 5'-AACTATA-CAAC-3' (SEQ ID NO:18) and the UR' was 5'-CTACTAC-CTCA-3' (SEQ ID NO:19). A single-stranded DNA oligonucleotide (2S), about 80 nucleotides, is provided to hybridize to the single-stranded portion of the DO to form a double-stranded hybridization complex, as illustrated in FIG. 4.

After hybridization, the region of the DR and UR can be represented as

```
5'-...TAAGAG-AACTATACAAC CTACTACCTCA-CGGAAC...-3'    SEQ ID NO: 20
       ||||||||| |||||||||||| |||||||||||  ||||||||
3'-...ATTCTC uugauauguug-gaugauggagu GCCTTG...-5'    SEQ ID NO: 21
``` where the target miRNA is in lowercase. Part of the DO is shown as the upper sequence, with the DR' in roman and the UR' underlined roman, flanked by sequence, partially shown, in italics, such as P1 or P2'. The bases in bolded italics represent the 3' end (on the left) and the 5' end (on the right) of the same 2S oligonucleotide.

After ligation, the portion shown forms a double-stranded structure without any nicks

```
5'-...TAAGAG-AACTATACAAC-CTACTACCTCA-CGGAAC...-3'    SEQ ID NO: 22
       ||||||||| |||||||||||| |||||||||||  ||||||||
3'-...ATTCTC-uugauauguug-gaugauggagu-GCCTTG...-5'    SEQ ID NO: 23
``` which is resistant to attack by exonucleases.

If the DO for let-7a becomes hybridized to similar let-7c, the following structure is formed:

```
5'-...TAAGAG-AACTATACAAC-CTACTACCTCA-CGGAAC...-3'    SEQ ID NO: 24
       ||||||||| |||||||||||| |||||||||||  ||||||||
3'-...ATTCTC-uugguauguug-gaugauggagu-GCCTTG...-5'    SEQ ID NO: 25
```

The complex, which contains a mismatch, can be nicked with a variety of enzymes, such as T4 endonuclease VII, T7 endonuclease I, or in combinations of exonuclease I and *E. coli* exonuclease III, S1 nuclease, or nuclease BAL-31. The nicked complex can then be degraded by treatment with a nuclease in step (b1) so that no ligation product is formed.

As illustrated, the covalently circularized, double-stranded structure can be linearized by treatment with a restriction endonuclease, if desired, where the 2S contains an appropriate restriction site. The linearized product can be amplified with primers.

Example 3b: Extended Detector Design for MicroRNAs

Extended detectors were designed for Let-7 family microRNAs that have been polyadenylated. The microRNAs are extended using polynucleotide adenylyltransferase to add a 3' polyadenine tail. For a Hsa let-7a microRNA (SEQ ID NO:10), a polyadenylated sequence is shown below (SEQ ID NO:28) in italics. An upstream detector is provided having SEQ ID NO:27 and an extended downstream detector is provided having SEQ ID NO:26, which has an italicized poly-T region (usually poly-dT if the detector is DNA).

```
5'-...TTTTTTTTAACTATAC AACCTACTACCTCA...-3'    SEQ ID NO: 26, 27
       |||||||||||||| ||||||||||||||
3'-aaaaauugauauug-uuggaugauggagu-5'            SEQ ID NO: 28
```

The combination of the supplemental 3' polyadenine tail and the extended poly-T region provides a longer complementary region for hybridization of the target to the detector, and allows greater freedom of designing DRs and URs for the target. For instance, the lengths of the complementary regions for the DD and UD can be more similar in length. When a family of related target sequences is being detected, a DD or UD can be used to detect more than one family member (a "generic detector"). Thus for Hsa let-7b,

```
5'-...TTTTTTTTAACCACAC AACCTACTACCTCA...-3'    SEQ ID NO: 29, 27
       |||||||||||||| ||||||||||||||
3'-aaaaauuggugug-uuggaugauggagu-5'             SEQ ID NO: 30
``` the same upstream detector can be used to detect let-7a and let-7b (and let-7c), since the 14 bases in the 5' direction are identical. Skilled artisans will be able to design various combinations of specific and generic detectors for related sequences, such as the let-7 family, depending on the number of detectors and hybridization properties desired.

After the extended detectors are allowed to hybridize to the polyadenylated microRNAs, the detectors are ligated to form the ligation product for detection or optional amplification. If the number of supplemental adenosines added is fewer than the number of dTs in the DD, this does not interfere with the ligation and subsequent steps. If the number of supplemental As is greater, then excess portion of the 3' tail need not hybridize entirely to the remaining 5' portion of the DD for specific and target-valid ligation to occur.

Example 4: Flap Design

Circularizable detector oligos were designed as in Example 3a, but where the UD has an additional poly-A CP5 sequence at the 5' end:

```
5'-AAAAA-CTACTACCTCA-CGGAAC...-3'    SEQ ID NO: 31
         |||||||||||  ||||||||
```

After hybridization of the DO to the target sequence, the UR' (underlined above) of the DO is hybridized to the target UR, but the poly-A sequence remains an unhybridized flap, as shown in FIG. 5a. The complex can be treated with a flap endonuclease, such as Fen-1, to remove the poly-A and the adjacent hybridized base. A DR' hybridized to an adjacent DR can be extended as in step (b0) of FIG. 1 and then ligated to the UR' region.

Alternatively, the DR' can have a noncomplementary portion (CP3), such as the single C underlined below:

5'-...*TAAGAG*-AACTATACAAC-<u>C</u>-3'       SEQ ID NO: 32
       ||||||||  ||||||||||| that can hybridize and fill the gap left by the endonuclease, as shown in FIG. 5d. After ligation, a nickless double-stranded complex is formed as in FIG. 5e. The circularized structure can be linearized, if desired, and amplified, as illustrated earlier in FIG. 4.

The headings provided above are intended only to facilitate navigation within the document and should not be used to characterize the meaning of one portion of text compared to another. Skilled artisans will appreciate that additional embodiments are within the scope of the invention. The invention is defined only by the following claims; limitations from the specification or its examples should not be imported into the claims.

We claim:

1. A method for detecting target nucleic acid sequences in a sample, wherein a target sequence has a downstream region (DR) and an upstream region (UR), comprising (a) contacting the sample with a pair of detector oligos, which pair comprises a downstream detector oligo (DD) having a complementary downstream region (DR') and a separate upstream detector oligo (UD) having a complementary upstream region (UR'), wherein at least one of the DD or UD has a second complementary region (DR2' or UR2') separated from the DR' or UR' by a noncomplementary region (CP1) that does not hybridize to the target nucleic acid, whereby the DR2' or UR2' can specifically hybridize to a DR2 or UR2 of the target nucleic acid, thereby allowing the pair of detectors to hybridize specifically to the target nucleic acids;

(b1) ligating the DR' and UR' if both are specifically hybridized to the DR and UR of a target sequence; and (b2) exposing hybridization complexes to at least one nuclease that degrades single strands but does not significantly degrade double strands,
whereby nonspecifically hybridized DDs and UDs are degraded by the nuclease;

whereby the ligation product indicates the presence of the target sequence in the sample.

2. The method of claim 1, wherein any of steps (a), (b1), or (b2) is performed in liquid phase.

3. The method of claim 1, wherein any of steps (a) (b1), or (b2) is performed while the target nucleic acid is attached to a solid surface.

4. The method of claim 1, wherein at least one of steps (a), (b1), or (b2) is performed by adding a reagent to the same reaction container as the preceding step.

5. The method of claim 1, wherein the target nucleic acid is a microRNA or a portion thereof.

6. The method of claim 5, wherein the microRNA or portion thereof is 3'-polyadenylated prior to step (a), and the DD has a poly-T region adjacent to the DR'.

7. The method of claim 1, wherein the sample has 0.1 ng nucleic acid or less.

8. The method of claim 1, wherein the nucleic acid is from fewer than 10 cells.

9. The method of claim 1, wherein the nuclease has 3'-to-5' activity.

10. The method of claim 1, wherein the nuclease has 5'-to-3' activity.

11. The method of claim 10, wherein the nuclease digests 5' flaps.

12. The method of claim 1, wherein the method further comprises (c) inactivating the nuclease.

13. The method of claim 2, wherein the target nucleic acid is in situ, and step (b1) or (b2) is performed in liquid phase.

14. The method of claim 3, wherein step (b1) or (b2) is performed in liquid phase.

15. The method of claim 1, wherein an attenuator oligonucleotide is further provided in step (a), wherein the attenuator comprises a sequence that is complementary to a portion of a DR2, DR2', UR2, or UR2' of a high-abundance target sequence (HAT).

16. The method of claim 15, wherein the attenuator
(i) comprises a sequence that is complementary to a portion of a DR2 of a HAT and a sequence that is complementary to a portion of a DR of the same HAT; or
(ii) comprises a sequence that is complementary to a portion of a UR of a HAT and a sequence that is complementary to a portion of a UR2 of the same HAT.

17. The method of claim 1, wherein (i) the DD has a 5'-exonuclease-blocking group, (ii) the UD has a 3'-exonuclease-blocking group, or both (i) and (ii).

18. The method of claim 1, wherein the DD has a 5'-terminal DR2' region that is hybridized to a DR2 protector oligo.

19. The method of claim 1, wherein the UD has a 3'-terminal UR2' region that is hybridized to a UR2 protector oligo.

20. The method of claim 1, wherein the DR and UR are separated by at least one nucleotide, and the method further comprises
(b0) extending the DR' using the sample as template.

21. The method of claim 1, further comprising the step of (d) amplifying the ligation products.

22. The method of claim 21, wherein the DD has a first amplification region (P1) downstream of the DR', and the UD has a second amplification region (P2') upstream of the UR'.

23. The method of claim 22, wherein step (b2) degrades nonhybridized P1 or P2' regions.

24. The method of claim 1, wherein
(i) the DR2' and DR' are separated by a noncomplementary region and
(ii) the UR2' and UR' are separated by another noncomplementary region.

25. The method of claim 1, wherein step (b1) is performed before step (b2).

26. The method of claim 1, wherein step (b1) is performed during step (b2).

27. The method of claim 1, wherein step (b1) is performed after step (b2).

28. The method of claim 1, further comprising the step of (e) detecting the ligation product.

29. The method of claim 28, wherein step (e) is performed by sequencing.

30. The method of claim 28, wherein step (e) is performed with a flow-through system for counting labeled molecules.

31. The method of claim 28, wherein step (e) is performed by qPCR.

32. The method of claim 1, wherein the target nucleic acid comprises an mRNA.

33. The method of claim 1, wherein the target nucleic acid comprises an siRNA, antisense RNA, or long noncoding RNA.

34. The method of claim 1, wherein a detector oligo has a locked nucleic acid (LNA) or a peptide nucleic acid (PNA) backbone at one or more positions.

35. The method of claim 1, wherein a detector oligo has an inverted nucleotide, a dideoxynucleotide, or a phosphorothioate bond.

36. The method of claim 1, wherein the sample is a tissue sample.

37. The method of claim 1, wherein the sample is mounted on a slide.

38. The method of claim 1, wherein the sample is a formalin-fixed, paraffin-embedded (FFPE) sample.

39. The method of claim 1, wherein the target nucleic acid is from an FFPE sample.

40. The method of claim 1, wherein the target nucleic acid is in situ.

41. The method of claim 1, wherein (i) sets of multiple DDs, each having different DR' regions, or (ii) sets of multiple UDs, each having different UR' regions, provide measurement of portions of the same target sequence.

42. The method of claim 1, further comprising the step of permeabilizing the cell walls, cell membranes, or subcellular structures.

43. The method of claim 1, further comprising the step of eluting the ligation product.

44. A kit for detecting a target nucleic acid sequence in a sample, wherein the target sequence has a downstream region (DR) and an upstream region (UR), comprising
a pair of detector oligos, which pair comprises
a downstream detector oligo (DD) having a complementary downstream region (DR') and a separate upstream detector oligo (UD) having a complementary upstream region (UR'), wherein at least one of the downstream detector (DD) or the upstream detector (UD) has a second complementary region (DR2' or UR2') separated from the DR' or UR' by a noncomplementary region (CP1) that does not hybridize to the target nucleic acid and that has an amplification region (P1 or P2'), whereby the DR2' or UR2' can specifically hybridize to a DR2 or UR2 of the target nucleic acid, and at least one nuclease.

45. The kit of claim 44, further comprising a ligase.

46. The kit of claim 44, further comprising a component for a reaction buffer for an enzyme in the kit, wherein the component is suitable for addition for the enzyme reaction in the same container as the preceding step of the method.

47. The kit of claim 44, wherein
   (i) the DR2' and DR' are separated by a noncomplementary region and
   (ii) the UR2' and UR' are separated by another noncomplementary region.

48. The kit of claim 44, wherein a detector oligo has a locked nucleic acid (LNA) or a peptide nucleic acid (PNA) backbone at one or more positions.

49. The kit of claim 44, wherein a detector oligo has an inverted nucleotide, a dideoxynucleotide, or a phosphorothioate bond.

50. The kit of claim 44, wherein the DD has a first amplification region (P1) downstream of the DR', and the UD has a second amplification region (P2') upstream of the UR'.

51. The kit of claim 44, further comprising an inhibitor to the nuclease.

52. The kit of claim 44, wherein the nuclease degrades single strands but does not significantly degrade double strands.

53. The kit of claim 44, wherein the DD has a poly-T region adjacent to the DR'.

54. The kit of claim 44, wherein (i) the DD has a 5'-exonuclease-blocking group, (ii) the UD has a 3'-exonuclease-blocking group, or both (i) and (ii).

55. The kit of claim 44, further comprising a DR2 protector oligo.

56. The kit of claim 44, further comprising a UR2 protector oligo.

57. The kit of claim 44, comprising (i) sets of multiple DDs, each having different DR' regions or (ii) sets of multiple UDs, each having different UR' regions, that are complementary to portions of the same target sequence.

58. The kit of claim 44, further comprising an eluent solution for removing oligonucleotides from a tissue sample.

59. The kit of claim 44, further comprising an attenuator oligonucleotide comprising a sequence that is complementary to a portion of a DR2, DR2', UR2, or UR2' of a high-abundance target sequence (HAT).

60. The kit of claim 59, wherein the attenuator
   (i) comprises a sequence that is complementary to a portion of a DR2 of a HAT and a sequence that is complementary to a portion of a DR of the same HAT; or
   (ii) comprises a sequence that is complementary to a portion of a UR of a HAT and a sequence that is complementary to a portion of a UR2 of the same HAT.

* * * * *